(12) United States Patent
Herrington et al.

(10) Patent No.: US 6,828,103 B2
(45) Date of Patent: Dec. 7, 2004

(54) GENETIC POLYMORPHISMS OF ESTROGEN RECEPTOR ALPHA ASSOCIATED WITH FAVORABLE RESPONSE TO HORMONE REPLACEMENT THERAPY

(75) Inventors: David M. Herrington, Winston-Salem, NC (US); Timothy D. Howard, Clemmons, NC (US); Gregory A. Hawkins, High Point, NC (US); Deborah A. Meyers, Mocksville, NC (US)

(73) Assignee: Wake Forest University, Winston-Salem, NC (US)

(*) Notice: Subject to any disclaimer, the term of this patent is extended or adjusted under 35 U.S.C. 154(b) by 138 days.

(21) Appl. No.: 10/081,563

(22) Filed: Feb. 22, 2002

(65) Prior Publication Data

US 2002/0187495 A1 Dec. 12, 2002

Related U.S. Application Data

(60) Provisional application No. 60/270,700, filed on Feb. 22, 2001.

(51) Int. Cl.[7] .......................... C12Q 1/68; C12P 19/34; G01N 33/00; C07H 21/04
(52) U.S. Cl. .................. 435/6; 435/91.1; 435/91.2; 436/94; 536/23.51; 536/24.31
(58) Field of Search .......................... 435/6, 7.1, 183, 435/91.1, 91.2; 436/501, 94; 530/350; 536/23.1, 23.5, 23.51, 24.31

(56) References Cited

PUBLICATIONS

Albagha et al., *Estrogen Receptor α Gene Polymorphisms and Bone Mineral Density: Haplotype Analysis in Women From the United Kingdom*, Journal of Bone and Mineral Research, vol. 16, No. 1, 2001, pp. 128–134.

Salmén et al., *The Protective Effect of Hormone–Replacement Therapy on Fracture Risk is Modulated by Estrogen Receptor α Genotype in Early Postmenopausal Women*, Journal of Bone and Mineral Research, vol. 15, No. 12, 2000, pp. 2479–2486.

Ongphiphadhanakul et al., *Oestrogen–Receptor–α Gene Polymorphism Affects Response in Bone Mineral Density to Oestrogen in Post–Menopausal Women*, Clinical Endocrinology, vol. 52, 2000, pp. 581–585.

Deng et al., *Association of Estrogen Receptor–α Genotypes With Body Mass Index in Normal Healthy Postmenopausal Caucasian Women*, The Journal of Clinical Endocrinology & Metabolism, vol. 85, No. 8, 2000, pp. 2748–2751.

Kikuchi et al., *Association of Serum Low–Density Lipoprotein Metabolism With Oestrogen Receptor Gene Polymorphisms in Health Children*, Acta Pædiatr, vol. 89, 2000, pp. 42–45.

Scohy et al., *Identification of an Enhancer and an Alternative Promoter in the First Intron of the α–Fetoprotein Gene*, Nucleic Acids Research, vol. 28, No. 19, 2000, pp. 3743–3751.

Han et al., *Non–Association of Estrogen Receptor Genotypes With Bone Mineral Density and Bone Turnover in Korean Pre–, Peri– and Postmenopausal Women*, Osteoporos Int, vol. 9, 1999, pp. 290–295.

(List continued on next page.)

Primary Examiner—Bradley L. Sisson
(74) Attorney, Agent, or Firm—Myers Bigel Sibley and Sajovec, P.A.

(57) ABSTRACT

A method of screening a subject for increased likelihood of having a favorable response to estrogen replacement therapy comprises detecting the presence of the rare form of at least one estrogen receptor alpha polymorphism in the subject, the presence of the estrogen receptor alpha polymorphism indicating the subject is more likely to have a favorable response to estrogen replacement therapy (e.g., with respect to cardiovascular health, heart disease, and/or HDL levels).

6 Claims, 3 Drawing Sheets

OTHER PUBLICATIONS

Schubert et al., *Single Nucleotide Polymorphisms (SNPs) in the Estrogen Receptor Gene and Breast Cancer Susceptibility*, Journal of Steroid Biochemistry & Molecular Biology, vol. 71, 1999, pp. 21–27.

Deng et al., *Change of Bone Mass in Postmenopausal Caucasian Women With and Without Hormone Replacement Therapy is Associated With Vitamin D Receptor and Estrogen Receptor Genotypes*, Hum Genet, vol. 103, 1998, pp. 576–585.

Jeng et al., *Estrogen Receptor Expression and Function in Long–Term Estrogen–Deprived Human Breast Cancer Cells*, Endocrinology, vol. 139, No. 10, 1998, pp. 4164–4174.

Sudhir et al., *Premature Coronary Artery Disease Associated With a Disruptive Mutation in the Estrogen Receptor Gene in a Man*, Circulation, vol. 96, No. 10, Nov. 18, 1997, pp. 3774–3777.

Han et al., *Nonassociation of Estrogen Receptor Genotypes With Bone Mineral Density and Estrogen Responsiveness to Hormone Replacement Therapy in Korean Postmenopausal Women*, Journal of Clinical Endocrinology and Metabolism, vol. 82, No. 4, 1997, pp. 991–995.

Matsubara et al., *Genotype Distribution of Estrogen Receptor Polymorphisms in Men and Postmenopausal Women From Healthy and Coronary Populations and Its Relation to Serum Lipid Levels*, Arteriosclerosis, Thrombosis, and Vascular Biology, vol. 17, No. 11, Nov. 1997, pp. 3006–3012.

Kobayashi et al., *Association of Bone Mineral Density With Polymorphism of the Estrogen Receptor Gene*, Journal of Bone and Mineral Research, vol. 11, No. 3, 1996, pp. 306–311.

Sano et al., *Association of Estrogen Receptor Dinucleotide Repeat Polymorphism With Osteoporosis*, Biochemical and Biophysical Research Communications, vol. 217, No. 1, Dec. 5, 1995, pp. 378–383.

Smith et al., *Estrogen Resistance Caused by a Mutation in the Estrogen–Receptor Gene in a Man*, The New England Journal of Medicine, vol. 331, No. 16, Oct. 20, 1994, pp. 1056–1061.

Schachter et al., *Re: "Risk of Miscarriage and a Common Variant of the Estrogen Receptor Gene"*, Am. J. Epidemio., vol. 140, 1994; pp. 1144–1145.

Yaich et al., *Analysis of the PvuII Restriction Fragment–Length Polymorphism and Exon Structure of the Estrogen Receptor Gene in Breast Cancer and Peripheral Blood*, Cancer Research, vol. 52, Jan. 1, 1992, pp. 77–83.

Berkowitz et al., *An Estrogen Receptor Genetic Polymorphism and the Risk of Primary and Secondary Recurrent Spontaneous Abortion*, Am., J. Obstet Gynecol., vol. 1761, No. 6, 1994, pp. 1579–1584.

Andersen et al., *Oestrogen Receptor (ESR) Polymorphisms and Breast Cancer Susceptibility*, Hum Genet, vol. 94, 1994, pp. 665–670.

Lehrer et al., *Estrogen Receptor Variant and Hypertension in Women*, Hypertension, vol. 21, No. 4, Apr. 1993, pp. 439–441.

del Sanno et al., *Dinucleotide Repeat Polymorphism in the Human Estrogen Receptor (ESR) Gene*, Human Molecular Genetics, vol. 1, No. 5, 1992, p. 354.

Lehrer et al., *Oestrogen Receptor B–Region Polymorphism and Spontaneous Abortion in Women With Breast Cancer*, The Lancet, Mar. 17, 1990, pp. 622–624.

Parl et al., *Genomic DNA Analysis of the Estrogen Receptor Gene in Breast Cancer*, Breast Cancer Research and Treatment, vol. 14, 1989, pp. 57–64.

Hill et al., *Estrogen Receptor Expression in Human Breast Cancer Associated With an Estrogen Receptor Gene Restriction Fragment Length Polymorphism*, Cancer Research, vol. 49, Jan. 1, 1989, pp. 145–148.

Castagnoli et al., *PvuII RFLP Inside the Human Estrogen Receptor Gene*, Nucleic Acids Research, vol. 15, No. 2, 1987, p. 866.

SEQUENCE LISTING

<160> NUMBER OF SEQ ID NOS: 25

<210> SEQ ID NO 1
<211> LENGTH: 6450
<212> TYPE: DNA
<213> ORGANISM: Homo sapiens
<220> FEATURE:
<221> NAME/KEY: CDS
<222> LOCATION: (361)..(2148)
<223> OTHER INFORMATION:
<300> PUBLICATION INFORMATION:
<308> DATABASE ACCESSION NUMBER: X03635
<309> DATABASE ENTRY DATE: 1993-09-12
<313> RELEVANT RESIDUES: (1)..(6450)

<400> SEQUENCE: 1

```
gagttgtgcc tggagtgatg tttaagccaa tgtcagggca aggcaacagt ccctggccgt        60
cctccagcac ctttgtaatg catatgagct cgggagacca gtacttaaag ttggaggccc       120
gggagcccag gagctggcgg agggcgttcg tcctgggagc tgcacttgct ccgtcgggtc       180
gccggcttca ccggaccgca ggctcccggg gcagggccgg ggccagagct cgcgtgtcgg       240
cgggacatgc gctgcgtcgc ctctaacctc gggctgtgct cttttccag gtggcccgcc       300 ggtttctgag ccttctgccc tgcggggaca cggtctgcac cctgccccgcg gccacggacc      360 atg acc atg acc ctc cac acc aaa gca tct ggg atg gcc cta ctg cat        408
Met Thr Met Thr Leu His Thr Lys Ala Ser Gly Met Ala Leu Leu His
1               5                   10                  15 cag atc caa ggg aac gag ctg gag ccc ctg aac cgt ccg cag ctc aag        456
Gln Ile Gln Gly Asn Glu Leu Glu Pro Leu Asn Arg Pro Gln Leu Lys
                20                  25                  30 atc ccc ctg gag cgg ccc ctg ggc gag gtg tac ctg gac agc agc aag        504
Ile Pro Leu Glu Arg Pro Leu Gly Glu Val Tyr Leu Asp Ser Ser Lys
```

-continued

```
               35                  40                  45
ccc gcc gtg tac aac tac ccc gag ggc gcc tac gag ttc aac gcc      552
Pro Ala Val Tyr Asn Tyr Pro Glu Gly Ala Ala Tyr Glu Phe Asn Ala
    50                  55                  60 gcg gcc gcc gcc aac gcg cag gtc tac ggt cag acc ggc ctc ccc tac  600
Ala Ala Ala Ala Asn Ala Gln Val Tyr Gly Gln Thr Gly Leu Pro Tyr
65              70                  75                  80 ggc ccc ggg tct gag gct gcg gcg ttc ggc tcc aac ggc ctg ggg ggt  648
Gly Pro Gly Ser Glu Ala Ala Ala Phe Gly Ser Asn Gly Leu Gly Gly
                85                  90                  95 ttc ccc cca ctc aac agc gtg tct ccg agc ccg ctg atg cta ctg cac  696
Phe Pro Pro Leu Asn Ser Val Ser Pro Ser Pro Leu Met Leu Leu His
            100                 105                 110 ccg ccg ccg cag ctg tcg cct ttc ctg cag ccc cac ggc cag cag gtg  744
Pro Pro Pro Gln Leu Ser Pro Phe Leu Gln Pro His Gly Gln Gln Val
        115                 120                 125 ccc tac tac ctg gag aac gag ccc agc ggc tac acg gtg cgc gag gcc  792
Pro Tyr Tyr Leu Glu Asn Glu Pro Ser Gly Tyr Thr Val Arg Glu Ala
    130                 135                 140 ggc ccg ccg gca ttc tac agg cca aat tca gat aat cga cgc cag ggt  840
Gly Pro Pro Ala Phe Tyr Arg Pro Asn Ser Asp Asn Arg Arg Gln Gly
145                 150                 155                 160 ggc aga gaa aga ttg gcc agt acc aat gac aag gga agt atg gct atg  888
Gly Arg Glu Arg Leu Ala Ser Thr Asn Asp Lys Gly Ser Met Ala Met
                165                 170                 175 gaa tct gcc aag gag act cgc tac tgt gca gtg tgc aat gac tat gct  936
Glu Ser Ala Lys Glu Thr Arg Tyr Cys Ala Val Cys Asn Asp Tyr Ala
            180                 185                 190 tca ggc tac cat tat gga gtc tgg tcc tgt gag ggc tgc aag gcc ttc  984
Ser Gly Tyr His Tyr Gly Val Trp Ser Cys Glu Gly Cys Lys Ala Phe
        195                 200                 205 ttc aag aga agt att caa gga cat aac gac tat atg tgt cca gcc acc  1032
Phe Lys Arg Ser Ile Gln Gly His Asn Asp Tyr Met Cys Pro Ala Thr
    210                 215                 220 aac cag tgc acc att gat aaa aac agg agg aag agc tgc cag gcc tgc  1080
Asn Gln Cys Thr Ile Asp Lys Asn Arg Arg Lys Ser Cys Gln Ala Cys
225                 230                 235                 240 cgg ctc cgc aaa tgc tac gaa gtg gga atg atg aaa ggt ggg ata cga  1128
Arg Leu Arg Lys Cys Tyr Glu Val Gly Met Met Lys Gly Gly Ile Arg
                245                 250                 255 aaa gac cga aga gga ggg aga atg ttg aaa cac aag cgc cag aga gat  1176
Lys Asp Arg Arg Gly Gly Arg Met Leu Lys His Lys Arg Gln Arg Asp
            260                 265                 270 gat ggg gag ggc agg ggt gaa gtg ggg tct gct gga gac atg aga gct  1224
Asp Gly Glu Gly Arg Gly Glu Val Gly Ser Ala Gly Asp Met Arg Ala
        275                 280                 285 gcc aac ctt tgg cca agc ccg ctc atg atc aaa cgc tct aag aag aac  1272
Ala Asn Leu Trp Pro Ser Pro Leu Met Ile Lys Arg Ser Lys Lys Asn
    290                 295                 300 agc ctg gcc ttg tcc ctg acg gcc gac cag atg gtc agt gcc ttg ttg  1320
Ser Leu Ala Leu Ser Leu Thr Ala Asp Gln Met Val Ser Ala Leu Leu
305                 310                 315                 320 gat gct gag ccc ccc ata ctc tat tcc gag tat gat cct acc aga ccc  1368
Asp Ala Glu Pro Pro Ile Leu Tyr Ser Glu Tyr Asp Pro Thr Arg Pro
                325                 330                 335 ttc agt gaa gct tcg atg atg ggc tta ctg acc aac ctg gca gac agg  1416
Phe Ser Glu Ala Ser Met Met Gly Leu Leu Thr Asn Leu Ala Asp Arg
            340                 345                 350 gag ctg gtt cac atg atc aac tgg gcg aag agg gtg cca ggc ttt gtg  1464
```

|   |   |
|---|---|
| Glu Leu Val His Met Ile Asn Trp Ala Lys Arg Val Pro Gly Phe Val<br>                355                          360                          365 |   |
| gat ttg acc ctc cat gat cag gtc cac ctt cta gaa tgt gcc tgg cta<br>Asp Leu Thr Leu His Asp Gln Val His Leu Leu Glu Cys Ala Trp Leu<br>       370                        375                          380 | 1512 |
| gag atc ctg atg att ggt ctc gtc tgg cgc tcc atg gag cac cca gtg<br>Glu Ile Leu Met Ile Gly Leu Val Trp Arg Ser Met Glu His Pro Val<br>385                         390                          395                          400 | 1560 |
| aag cta ctg ttt gct cct aac ttg ctc ttg gac agg aac cag gga aaa<br>Lys Leu Leu Phe Ala Pro Asn Leu Leu Leu Asp Arg Asn Gln Gly Lys<br>                405                          410                          415 | 1608 |
| tgt gta gag ggc atg gtg gag atc ttc gac atg ctg ctg gct aca tca<br>Cys Val Glu Gly Met Val Glu Ile Phe Asp Met Leu Leu Ala Thr Ser<br>                420                          425                          430 | 1656 |
| tct cgg ttc cgc atg atg aat ctg cag gga gag gag ttt gtg tgc ctc<br>Ser Arg Phe Arg Met Met Asn Leu Gln Gly Glu Glu Phe Val Cys Leu<br>                435                          440                          445 | 1704 |
| aaa tct att att ttg ctt aat tct gga gtg tac aca ttt ctg tcc agc<br>Lys Ser Ile Ile Leu Leu Asn Ser Gly Val Tyr Thr Phe Leu Ser Ser<br>       450                        455                          460 | 1752 |
| acc ctg aag tct ctg gaa gag aag gac cat atc cac cga gtc ctg gac<br>Thr Leu Lys Ser Leu Glu Glu Lys Asp His Ile His Arg Val Leu Asp<br>465                         470                          475                          480 | 1800 |
| aag atc aca gac act ttg atc cac ctg atg gcc aag gca ggc ctg acc<br>Lys Ile Thr Asp Thr Leu Ile His Leu Met Ala Lys Ala Gly Leu Thr<br>                485                          490                          495 | 1848 |
| ctg cag cag cag cac cag cgg ctg gcc cag ctc ctc ctc atc ctc tcc<br>Leu Gln Gln Gln His Gln Arg Leu Ala Gln Leu Leu Leu Ile Leu Ser<br>                500                          505                          510 | 1896 |
| cac atc agg cac atg agt aac aaa ggc atg gag cat ctg tac agc atg<br>His Ile Arg His Met Ser Asn Lys Gly Met Glu His Leu Tyr Ser Met<br>                515                          520                          525 | 1944 |
| aag tgc aag aac gtg gtg ccc ctc tat gac ctg ctg ctg gag atg ctg<br>Lys Cys Lys Asn Val Val Pro Leu Tyr Asp Leu Leu Leu Glu Met Leu<br>       530                        535                          540 | 1992 |
| gac gcc cac cgc cta cat gcg ccc act agc cgt gga ggg gca tcc gtg<br>Asp Ala His Arg Leu His Ala Pro Thr Ser Arg Gly Gly Ala Ser Val<br>545                         550                          555                          560 | 2040 |
| gag gag acg gac caa agc cac ttg gcc act gcg ggc tct act tca tcg<br>Glu Glu Thr Asp Gln Ser His Leu Ala Thr Ala Gly Ser Thr Ser Ser<br>                565                          570                          575 | 2088 |
| cat tcc ttg caa aag tat tac atc acg ggg gag gca gag ggt ttc cct<br>His Ser Leu Gln Lys Tyr Tyr Ile Thr Gly Glu Ala Glu Gly Phe Pro<br>       580                        585                          590 | 2136 |
| gcc aca gtc tga gagctccctg gctcccacac ggttcagata atccctgctg<br>Ala Thr Val<br>            595 | 2188 |
| cattttaccc tcatcatgca ccactttagc caaattctgt ctcctgcata cactccggca | 2248 |
| tgcatccaac accaatggct ttctagatga gtggccattc atttgcttgc tcagttctta | 2308 |
| gtggcacatc ttctgtcttc tgttgggaac agccaaaggg attccaaggc taaatctttg | 2368 |
| taacagctct cttctcccct tgctatgtta ctaagcgtga ggattcccgt agctcttcac | 2428 |
| agctgaactc agtctatggg ttggggctca gataactctg tgcatttaag ctacttgtag | 2488 |
| agacccaggc ctggagagta gacattttgc ctctgataag cactttttaa atggctctaa | 2548 |
| gaataagcca cagcaaagaa tttaaagtgg ctcctttaat tggtgacttg gagaaagcta | 2608 |
| ggtcaagggt ttattatagc accctcttgt attcctatgg caatgcatcc ttttatgaaa | 2668 |

```
gtggtacacc ttaaagcttt tatatgactg tagcagagta tctggtgatt gtcaattcac    2728 ttcccectat aggaatacaa ggggccacac agggaaggca gatcccctag ttggccaaga    2788 cttatttaa cttgatacac tgcagattca gagtgtcctg aagctctgcc tctggctttc    2848
cggtcatggg ttccagttaa ttcatgcctc ccatggacct atggagagca acaagttgat    2908
cttagttaag tctccctata tgagggataa gttcctgatt tttgttttta ttttgtgtt    2968 acaaaagaaa gccctccctc cctgaacttg cagtaaggtc agcttcagga cctgttccag    3028
tgggcactgt acttggatct tcccggcgtg tgtgtgcctt acacaggggt gaactgttca    3088
ctgtggtgat gcatgatgag ggtaaatggt agttgaaagg agcaggggcc ctggtgttgc    3148
atttagccct ggggcatgga gctgaacagt acttgtgcag gattgttgtg gctactagag    3208
aacaagaggg aaagtagggc agaaactgga tacagttctg agcacagcca gacttgctca    3268
ggtggccctg cacaggctgc agctacctag gaacattcct tgcagacccc gcattgcctt    3328 tggggtgcc ctgggatccc tggggtagtc cagctcttat tcatttccca gcgtggccct    3388
ggttggaaga agcagctgtc aagttgtaga cagctgtgtt cctacaattg cccagcacc    3448 ctggggcacg ggagaagggt ggggaccgtt gctgtcacta ctcaggctga ctggggcctg    3508
gtcagattac gtatgcccct ggtggtttag agataatcca aaatcagggt ttggtttggg    3568
gaagaaaatc ctccccccttc ctccccgcc ccgttcccta ccgcctccac tcctgccagc    3628
tcatttcctt caatttcctt tgacctatag gctaaaaaag aaaggctcat tccagccaca    3688
gggcagcctt ccctgggcct ttgcttctct agcacaatta tgggttactt ccttttttctt    3748 aacaaaaag aatgtttgat ttcctctggg tgaccttatt gtctgtaatt gaaaccctat    3808
tgagaggtga tgtctgtgtt agccaatgac ccaggtagct gctcgggctt ctcttggtat    3868
gtcttgtttg gaaaagtgga tttcattcat ttctgattgt ccagttaagt gatcaccaaa    3928
ggactgagaa tctgggaggg caaaaaaaaa aaaaaaagtt tttatgtgca cttaaatttg    3988
gggacaattt tatgtatctg tgttaaggat atgcttaaga acataattct tttgttgctg    4048
tttgtttaag aagcaccta gtttgtttaa gaagcacctt atatagtata atatatattt    4108
ttttgaaatt acattgcttg tttatcagac aattgaatgt agtaattctg ttctggattt    4168
aatttgactg ggttaacatg caaaaaccaa ggaaaaatat ttagttttttt tttttttttt    4228 tgtatacttt tcaagctacc ttgtcatgta tacagtcatt tatgcctaaa gcctggtgat    4288
tattcattta aatgaagatc acatttcata tcaacttttg tatccacagt agacaaaata    4348
gcactaatcc agatgcctat tgttggatat tgaatgacag acaatcttat gtagcaaaga    4408
ttatgcctga aaaggaaaat tattcagggc agctaatttt gcttttacca aaatatcagt    4468
agtaatattt ttggacagta gctaatgggt cagtgggttc ttttaatgt ttatacttag    4528 atttctttt aaaaaatta aataaaaca aaaaaattt ctaggactag acgatgtaat    4588
accagctaaa gccaaacaat tatacagtgg aaggttttac attattcatc caatgtgttt    4648
ctattcatgt taagatacta ctacatttga agtgggcaga gaacatcaga tgattgaaat    4708
gttcgcccag gggtctccag caactttgga atctctttg tatttttact tgaagtgcca    4768
ctaatggaca gcagatattt tctggctgat gttggtattg ggtgtaggaa catgatttaa    4828
aaaaaaaact cttgcctctg cttttcccca ctctgaggca agttaaaatg taaaagatgt    4888
gatttatctg gggggctcag gtatggtggg gaagtggatt caggaatctg ggaatggca    4948 aatatattaa gaagagtatt gaaagtattt ggaggaaaat ggttaattct gggtgtgcac    5008
caaggttcag tagagtccac ttctgccctg gagaccacaa atcaactagc tccatttaca    5068
```

```
gccatttcta aaatggcagc ttcagttcta gagaagaaag aacaacatca gcagtaaagt    5128
ccatggaata gctagtggtc tgtgtttctt ttcgccattg cctagcttgc cgtaatgatt    5188
ctataatgcc atcatgcagc aattatgaga ggctaggtca tccaaagaga agaccctatc    5248
aatgtaggtt gcaaaatcta acccctaagg aagtgcagtc tttgatttga tttccctagt    5308
aaccttgcag atatgtttaa ccaagccata gcccatgcct tttgagggct gaacaaataa    5368
gggacttact gataatttac ttttgatcac attaaggtgt tctcaccttg aaatcttata    5428
cactgaaatg gccattgatt taggccactg gcttagagta ctccttcccc tgcatgacac    5488
tgattacaaa tactttccta ttcatacttt ccaattatga gatggactgt gggtactggg    5548
agtgatcact aacaccatag taatgtctaa tattcacagg cagatctgct tggggaagct    5608
agttatgtga aaggcaaata aagtcataca gtagctcaaa aggcaaccat aattctcttt    5668
ggtgcaagtc ttgggagcgt gatctagatt acactgcacc attcccaagt taatcccctg    5728
aaaacttact ctcaactgga gcaaatgaac tttggtccca aatatccatc ttttcagtag    5788
cgttaattat gctctgtttc caactgcatt tcctttccaa ttgaattaaa gtgtggcctc    5848
gtttttagtc atttaaaatt gttttctaag taattgctgc ctctattatg gcacttcaat    5908
tttgcactgt cttttgagat tcaagaaaaa tttctattca tttttttgca tccaattgtg    5968
cctgaacttt taaaatatgt aaatgctgcc atgttccaaa cccatcgtca gtgtgtgtgt    6028
ttagagctgt gcaccctaga aacaacatac ttgtcccatg agcaggtgcc tgagacacag    6088 accccttgc attcacagag aggtcattgg ttatagagac ttgaattaat aagtgacatt    6148
atgccagttt ctgttctctc acaggtgata aacaatgctt tttgtgcact acatactctt    6208
cagtgtagag ctcttgtttt atgggaaaag gctcaaatgc caaattgtgt ttgatggatt    6268
aatatgccct tttgccgatg catactatta ctgatgtgac tcggttttgt cgcagctttg    6328
ctttgtttaa tgaaacacac ttgtaaacct cttttgcact ttgaaaaaga atccagcggg    6388
atgctcgagc acctgtaaac aatttttctca acctatttga tgttcaaata aagaattaaa    6448
ct                                                                   6450
```

<210> SEQ ID NO 2
<211> LENGTH: 595
<212> TYPE: PRT
<213> ORGANISM: Homo sapiens

<400> SEQUENCE: 2

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
```

-continued

```
            115                 120                 125
Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
530                 535                 540
```

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 3
<211> LENGTH: 355
<212> TYPE: DNA
<213> ORGANISM: Homo sapiens

<400> SEQUENCE: 3
caaaatgtca ggataaagtg gatctgctgc atctcccaga gagtgcatgt tttgcttttc        60
taatgttaat ggatttactg tttttttccc cccaggccaa attcagataa tcgacgccag       120
ggtggcagag aaagattggc cagtaccaat gacaagggaa gtatggctat ggaatctgcc       180
aaggagactc gctactgtgc agtgtgcaat gactatgctt caggctacca ttatggagtc       240
tggtcctgtg agggctgcaa ggccttcttc aagagaagta ttcaaggtaa tagtgtgttg       300
aaaacgactt ctattttga tcctatgagc agatcctaag agccaaagcg actga            355

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 4
gcttcagcta catttgcata ttg                                                23

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
acctcaggtc acgaaccaaa g                                                  21

<210> SEQ ID NO 6
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 6
ccgagaagat cgagttgtag gac                                                23

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7

```
tcctcgttgg ctagaaatac g                                            21
```

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8

```
ggtggtgaaa tggaaagaga tg                                           22
```

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 9

```
atattggccc aggacttggc ag                                           22
```

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10

```
cacaggaacc ttcactccat c                                            21
```

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11

```
gcagagaagt ccaacaaagc a                                            21
```

<210> SEQ ID NO 12
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 12

```
cattggtctc taatggttct gaa                                          23
```

<210> SEQ ID NO 13
<211> LENGTH: 24
<212> TYPE: DNA
<213> ORGANISM: Artificial sequence
<220> FEATURE:
<223> OTHER INFORMATION: Syntheticoligonculetide

<400> SEQUENCE: 13

```
tctccatgtt tctaccaaag atac                                         24
```

<210> SEQ ID NO 14
<211> LENGTH: 33
<212> TYPE: DNA
<213> ORGANISM: Artificial sequence

```
<220> FEATURE:
<223> OTHER INFORMATION: Synthetic oligonucleotide

<400> SEQUENCE: 14
tctttctctg ccaccctggc gtcgattatc tga                                    33

<210> SEQ ID NO 15
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 15
ctgccaccct atctgtatct tttcctattc tcc                                    33

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
tgggctggca ggagatta                                                     18

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
gctgcgttca gagtcaartt c                                                 21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
ggctgaagat gcacactgaa t                                                 21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
ctggcatgtg acttctgaca g                                                 21

<210> SEQ ID NO 20
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 20
tgccacccta tctgtatctt ttc                                               23
```

```
<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
atcatagcct actgcagcct c                                              21

<210> SEQ ID NO 22
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 22
aattagctga gaatggtgat gtgt                                           24

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
acaattattt cagaaccatt a                                              21

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
ctttctctgc caccctggcg t                                              21

<210> SEQ ID NO 25
<211> LENGTH: 42000
<212> TYPE: DNA
<213> ORGANISM: Homo sapiens
<220> FEATURE:
<221> NAME/KEY: misc_feature
<222> LOCATION: (1)..(42000)
<223> OTHER INFORMATION: Nucleotides c5435870 - 53932871 of NT_023451.8
<221> NAME/KEY: exon
<222> LOCATION: (3372)..(3823)
<223> OTHER INFORMATION: Exon 1
<221> NAME/KEY: Intron
<222> LOCATION: (3824)..(38055)
<223> OTHER INFORMATION: Intron 1
<221> NAME/KEY: exon
<222> LOCATION: (38056)..(38246)
<223> OTHER INFORMATION: Exon 2

<400> SEQUENCE: 25
gactatggag agagctctcc tgtgctcaaa cactgcaata ctgggggtct ttcaaagcac    60
aaaaacatat atttgcatga tggcatcatt aacattttta tggctttcta tttcttttt   120 gtactggtct caagagccac tcataaatct ctcagtaact gcatagtgtc ccagggccag   180
agaccggcca ctcctggcat tgtgattaga gtcatttaat atccaaggtg gtgactaatg   240
tctggcaaca aagcctccat tgggtgtcat gtgtcctggg accctgagcg tgggcactct   300
```

-continued

```
aggagcacct cagtattgcg tgttagtact atggccgaga gaatagttga gaaagtggtc     360
aagaggtgga tccatgtgaa cgccactggg aaatgagaga cctcgttccc aatcacggtc     420
agtgcaactc gaaagcctaa aatcagttta aaacaaaggt atctacccttt atcttatgtt    480 catatcctag gcttttaata atacgtattt ttcacatgtt tacagaaagc agtcaactga     540
gctattcatg gaaggtttg tgggtttggt taacgaagtg gaggagtatt acatttcagc      600
tggaaacaca tccctagaat gccaaaacat ttattccaaa gtctggtttc ctggtgcaat    660
cggaggcatg gcaatgcctc tgttcagaga ctgggggcta gggccagtaa ggcatttgat    720
ccacatgtat cccagaaggc ttttattgtt aaattatatt ctttcggaaa aaccacccat    780
gtcctatttt gtaaacttga tatccataca cttttgactg gcattctatt ttagccgtaa    840
gactatgatt cacagcaagc ctgttttcc tcttgcttgg ggtggcagca gaaagcatag      900
ggtactttcc agcctccaag ggtaggggca aggggctgg ggtttctcct ccccagtaca      960
gctttctctg gctgtgccac actgctccct gtgagcagac agcaagtctc ccctcactcc    1020
ccactgccat tcatccagcg ctgtgcagta gcccagctgc gtgtctgccg ggagggctg     1080 ccaagtgccc tgcctactgg ctgcttccg aatccctgcc attccacgca aaacacatc      1140 cacacactct ctctgcctag ttcacacact gagccactcg cacatgcgag cacattcctt    1200
ccttccttct cactctctcg gcccttgact tctacaagcc catggaacat ttctggaaag    1260
acgttcttga tccagcaggg taggcttgtt ttgatttctc tctctgtagc tttagcattt    1320
tgagaaagca acttacccttt ctggctagtg tctgtatcct agcagggaga tgaggattgc   1380
tgttctccat gggggtatgt gtgtgtctcc ttttctttc aggacttgta ggattctttg     1440
tgccatttgc atataatttg gcaggttcac attttttaag agccctatga agtgcttttt    1500
gcatgtgttt taaaaaggca tttgaaaatt gaaagtgtga tttatggaaa ttaaatcatc    1560
tgtaaaaaat tgctttggaa agtaatgatt gctggccata aagggaaata tctgcgatgc    1620
acctaatgtg ttttttaaccc tttatttgct gacaatctat agtcattaat gctaaactcg    1680
attttggctt cagctacatt tgcatattgt ccaacaatgg tctattttg taagaattag     1740 ataaaatgta tacttgatat aaaatagtca aaaatgtaac tcttagtaac agtaagcttg    1800
gcatttagat agaccatgaa cacttcgtca gatactctgt tgggtgtttg ggatagcaat    1860
taaaacaaag tattgatagt tgtatcagag tctattaggc tgcagcaaag gaagtttatt    1920
caaaagtata aactatccaa gattatagac gcatgatata cttcacctat tttttgtctc    1980
cttaatatgt atatatatat atatatatat atatatacac atatatgtgt gtgtgtatgt    2040
gcgtgtgcat gtttaacttt taattcagtt aaaaacttttt ttctatttgt ttttcatctg   2100
gatatttgat tctgcatatc ctagcccaag tgaaccgaga agatcgagtt gtaggactaa    2160
aggatagaca tgcagaaatg cattttaaaa atctgttagc tggaccagac cgacaatgta    2220
acataattgc caaagctttg gttcgtgacc tgaggttatg tttggtatga aaaggtcaca    2280
ttttatattc agttttctga agttttggtt gcataaccaa cctgtggaag gcatgaacac    2340
ccatgtgcgc cctaaccaaa ggttttttctg aatcatcctt cacatgagaa ttcctaatgg   2400
gaccaagtac agtactgtgg tccaacataa acacacaagt caggctgaga gaatctcaga    2460
aggttgtgga agggtctatc tactttggga gcatttgca gaggaagaaa ctgaggtcct     2520
ggcaggttgc attcctctga tgcaaaatg cagctcttcc tatatgtata ccctgaatct     2580 ccgcccctt cccctcagat gcccctgtc agttccccca gctgctaaat atagctgtct      2640
gtggctggct gcgtatgcaa ccgcacaccc cattctatct gccctatctc ggttacagtg    2700
```

-continued

```
tagtcctccc cagggtcatc ctatgtacac actacgtatt tctagccaac gaggaggggg    2760
aatcaaacag aaagagagac aaacagagat atatcggagt ctggcacggg gcacataagg    2820
cagcacatta gagaaagccg gcccctggat ccgtctttcg cgtttatttt aagcccagtc    2880
ttccctgggc cacctttagc agatcctcgt gcgccccgc cccctggccg tgaaactcag     2940
cctctatcca gcagcgacga caagtaaagt aaagttcagg gaagctgctc tttgggatcg    3000
ctccaaatcg agttgtgcct ggagtgatgt ttaagccaat gtcagggcaa ggcaacagtc    3060
cctggccgtc ctccagcacc tttgtaatgc atatgagctc gggagaccag tacttaaagt    3120
tggaggcccg ggagcccagg agctggcgga gggcgttcgt cctgggactg cacttgctcc    3180
cgtcgggtcg cccggcttca ccggaccccg aggctcccgg ggcagggccg gggccagagc    3240
tcgcgtgtcg gcgggacatg cgctgcgtcg cctctaacct cgggctgtgc tcttttcca    3300 ggtggcccgc cggtttctga gccttctgcc ctgcggggac acggtctgca ccctgcccgc    3360
```

| | | |
|---|---|---|
| ggccacggac c atg acc atg acc ctc cac acc aaa gca tct ggg atg gcc<br>Met Thr Met Thr Leu His Thr Lys Ala Ser Gly Met Ala<br>1           5                   10 | | 3410 |
| cta ctg cat cag atc caa ggg aac gag ctg gag ccc ctg aac cgt ccg<br>Leu Leu His Gln Ile Gln Gly Asn Glu Leu Glu Pro Leu Asn Arg Pro<br>    15              20                  25 | | 3458 |
| cag ctc aag atc ccc ctg gag cgg ccc ctg ggc gag gtg tac ctg gac<br>Gln Leu Lys Ile Pro Leu Glu Arg Pro Leu Gly Glu Val Tyr Leu Asp<br>30              35                  40                  45 | | 3506 |
| agc agc aag ccc gcc gtg tac aac tac ccc gag ggc gcc gcc tac gag<br>Ser Ser Lys Pro Ala Val Tyr Asn Tyr Pro Glu Gly Ala Ala Tyr Glu<br>            50                  55                  60 | | 3554 |
| ttc aac gcc gcg gcc gcc gcc aac gcg cag gtc tac ggt cag acc ggc<br>Phe Asn Ala Ala Ala Ala Ala Asn Ala Gln Val Tyr Gly Gln Thr Gly<br>        65                  70                  75 | | 3602 |
| ctc ccc tac ggc ccc ggg tct gag gct gcg gcg ttc ggc tcc aac ggc<br>Leu Pro Tyr Gly Pro Gly Ser Glu Ala Ala Ala Phe Gly Ser Asn Gly<br>    80                  85                  90 | | 3650 |
| ctg ggg ggt ttc ccc cca ctc aac agc gtg tct ccg agc ccg ctg atg<br>Leu Gly Gly Phe Pro Pro Leu Asn Ser Val Ser Pro Ser Pro Leu Met<br>95                  100                 105 | | 3698 |
| cta ctg cac ccg ccg ccg cag ctg tcg cct ttc ctg cag ccc cac ggc<br>Leu Leu His Pro Pro Pro Gln Leu Ser Pro Phe Leu Gln Pro His Gly<br>110                 115                 120                 125 | | 3746 |
| cag cag gtg ccc tac tac ctg gag aac gag ccc agc ggc tac acg gtg<br>Gln Gln Val Pro Tyr Tyr Leu Glu Asn Glu Pro Ser Gly Tyr Thr Val<br>            130                 135                 140 | | 3794 |
| cgc gag gcc ggc ccg ccg gca ttc tac ag gtacccgcgc cgcgccgcc<br>Arg Glu Ala Gly Pro Pro Ala Phe Tyr Arg<br>        145                 150 | | 3843 |

```
cgtcggggtg gccgccgcgc ccggcaggag ggagggaggg agggagggag aagggagagc    3903
ctagggagct gcgggagccg cgggacgcgc gacccgaggg tgcgcgcagg gagcccgggg    3963
cgcgcggccc agcccggggg ttctgcgtgc agcccgcgct gcgttcagag tcaagttctc    4023
tcgccgggca gctgaaaaaa acgtactctc cacccactta ccgtccgtgc gagaggcaga    4083
cccgaaagcc cgggcttcct aacaaaacac acgttggaaa accagacaaa gcagcagtta    4143
tttgtggggg aaaacacctc caggcaaata aacacgggc gctttgagtc acttgggaag     4203
gtctcgctct tggcatttaa agttgggggt gtttggagtt agcagagctc agcagagttt    4263
tatttatcct tttaatgttt ttgttttaatg tgctccccaa atttcctttc atctagacta   4323
```

```
tttgattgga aatatgtcag ctatgatgat gactttctgg gaagcgattc ctgtcacccg    4383
cttttccctc ctccccaccc cacgtcctgg ggctttagag agcgattggg agttgaatgg    4443
gtctgatttc ggagttagct ggctgagtcc gcgctggagc ggattgctgg catgtgactt    4503
ctgacagccg gaaatttgta ggtgtcccgc gagtttaaaa caagccatat ggaagcacaa    4563
gtgcttaaaa ataatctcct gccagcccag tgacaagcct gtcccacccg gggagaatgc    4623
cccggagtgg cgtgcgggtc agccagggtc tgcgcctcgc agccactgtg gaaggagcgc    4683
ggccggtcca ggacacagga gaccactttg tgacttcaat ggcgaaggtt gtgtgtcctc    4743
attttaattt ttttccctac aagaattgtt ctttctccct ctcctctccc tcccattttc    4803
tcttgcccag tttctccttt tgttttttgt tttttgtttt cctgatgggc ctgcagaggg    4863
attaggtggg cgcttctggt gaacaccttc ctaggtggcc acaggacagg tgtaccccgg    4923
actgggtttg gaagcttcag ggcgccacat ggctgggtcc tgaattaggc atttcccaac    4983
tgtacactgg tatccggact ggtgtcccta tatctttctg ccttgtaagc cgtggaccaa    5043
tttttgttca gtattctgtt tccagggata tttatagcag aaggaagggg actaaagtgc    5103
agtttggccc cagaggatac tgaagggcag attctggggg tattcagtgt gcatcttcag    5163
ccgccttgga gaaatttaga gcatcccaca gccacgcaga tccaagctgt ctttactcaa    5223
aagacaaaca atgaacaaaa cttttaaagg ttggcatatt tcaaattaat tttacttgtt    5283
ttaatttagg gttaaaacag agaaaaagga tttcttctgc ccacctttt ttttttaaat    5343 ggaagaacaa agtacagcga ttaagtctaa ttccacacaa catttaaaac tgcttgatgt    5403
gaaggaaggc actggtatga tgtgaattcc ataaccttat gatggactcc agaaaccatt    5463
ttcttcccta tttaattttc agttctttta ttgcaaatta atgctgctga atttcaatgg    5523
gcactaatga gactgctcct tggtagatta tttactgcct tgctaataat tacaaagtga    5583
acctggtcaa atacagaggg gatcgcatct tattcaaaat tgttcatcat cccagtgata    5643
agtggtatca gtgtaatatg ccctatctta cactttctgc attacatgat attcaaacac    5703
tcttagaata ataaaaaaag agacaaggaa cttaaaaatt aaaaaaaaaa cttgcacaaa    5763
tgggactctg tgtggaaatt cagttttaga atgattttc ctgtgtttta tttcccggat    5823
tatctttcct cttttgttag aattctgcct gttattatcc agcaaggaaa agaagcatct    5883
atgcaagttc ttcatatgga cagatattat ttagtatttt tcccctctca gttttctgc    5943 ttaaatgact ctgggtataa aggaaaggat tgattggct cttttaggaa actttaagtt    6003
tcttaagtag ttctcaaaag ttttgggct gaaagcagtg ttttcaaact gcttgtcatg    6063
acccagaggg tcatgaactc agtttagtga gtctagaata ttttttaaaa ggactaaaat    6123
ggaaaggaat ataatagaaa atatcagagt gcatggtatt tcgtaaggat aagttttgtt    6183
tcctgaaaat ctgttttaat tatatgtgct tctgtgtgct gattgtgatg taaaatgtat    6243
ttcttactgt ggattgaatt caagaaaaaa attagaaagc taatggccta aaatattata    6303
tgttcagtag aaaacaaaaa attcaggcaa gtggctggtt gttttaccct atacaaatca    6363
aaaggctatt ttgattgtct tcatttcccc cttataaatt aggttggtgt ctttagtcat    6423
ttaggctaag ttttactatc tgattcttaa cttttctatt gtagaatggt gctgtcatgt    6483
ggactgtcct cccgagtgtc ccactggatg ttcagaaat ttatgtgaag gtcacgtcat    6543
ttagcattga gatgctgtgg ttaccttctt ccatttcttc cataatatgc agccacatct    6603
atgtgtgaag aaatgtaata gataaaattt ctctggacgc ataataatgt gagaaagatt    6663
gtcacatgtc ccagcaaatt gttattaata taaatttgtt acttggcaag ctgagatttt    6723
```

```
gcaagatgtt actcaaaatt tcacaatgaa ggaaacaggg agtcatctta tcctgggttc    6783
cttttttaga tttcaaacaa cttaggaact ttgaataaaa ctaaagatga agcttaacta    6843
tatcaactat cctttttaaa gttctaatta ggaatttaat gctgcatgct tatttcagtt    6903
ttattactca gtattcttaa aagttagacg tctctcactt ctccaaaaaa cttggcaaat    6963
gtataaatct tttgcatcaa aatcaatgcc ctgctaattt gtatcctggc catctgcata    7023
ttttggacaa ctaattttc cactggtgat catttgaaac tctttctcaa ctttgaatag     7083
agactgattt ccaaagtgag atttaagtga ctaagtttca agtttccgat acattttcc     7143 ttttacttag ataacatttc agccccttc ctttctgatc ttactttttt attaatttaa    7203
attgttactg attacgtgac actttgtgct ggtctaagaa tagtccagag tcacatattc    7263
cctggtgaat gagcatattt tcggatgaaa acggaatcac atcttcaatc cccatttcat    7323
tttcacctcc tccatgtggc ttgtacctgt tggaagaaa gctcctgaag gataattgcc     7383
acttattcta atctttctca cactcattta atttggatcc ctggctaaag ttgttattta    7443
cttttgtgat tatacttagt ctatgacatt cataatttgg gaaaattctc aggtttgaga    7503
attttggcgg cttgggattt cttttagttt cttatagttt taaggatatg taagacaggt    7563
gtaagaaact gccaagggga ggaaccatag atatcaggaa aaactagaaa agatgccaga    7623
cttaccatta atgaatgatg agacaatagt aactttgtta agtgagattg tatatgtgaa    7683
agtggtatag aaactaaaca aacattaggt gtttttatta ttttactcac atgttaatat    7743
ttgttttggt gctttcatag gctaaaaagc tgggaaataa cagatttaag tggtcaggaa    7803
ttttgttata aatatagaat gatgattata tgaaatcttt tcctgtgaaa gtcaaattta    7863
agtaaaatct ttatcaccat ctgcaacatt tgtctgcagc ctggcttacc aggttatcat    7923
aaagaacatt tattttacag atacattaaa gaaagtcaaa accctgatta tgtgtaaaca    7983
attttacata aggaaatata tgaatttta ttatattttt ctaaaatccg tactcagcat     8043
gaaattaata catcttaacc cctccctgtg acttcattat tatttttaat gtaactttag    8103
aagaacccag tagagagagc agcgtgctaa gtgtgtttct ttcttttcca gacaactttg    8163
aatggagagg agcaaattag tcttttggtt taattctgtc tcagtttgct tatctaaaga    8223
aaggaaaaca gagtggctac acttgtttag aaccatatgc atactccaga gaaagatgct    8283
ctattaatcc aaaaaatata gccacttgaa accagccaaa gcgaaagtgt aagggacttc    8343
atggaaagga ggcagttcac caaagttatt gaggggtttt atattttaaa ctccgccagt    8403
gaattgacgt gtaatgtcac ttacaaaaaa aaaaaagta tgtctgagct gttcgctact     8463
tcgtctctaa aatatactca tactgatctc tgaaatccca gaatttaagt gggctggagg    8523
ttacgggaag cacctttata atatccttaa tctcatgagg gaagaaacca taattgctga    8583
attctctgcc ttggataata tcaggaggga ctctgaagaa agttttgcag taatcaacaa    8643
tgttttaaat tatgtgtata tttttagatc acctcaaaaa atataggaag cacagaatga    8703
caactattct ggtctcaact gacacaattt tatgtagttt aataaagtaa taatttcaag    8763
aaacgtgggc aaataagaaa gagtatgact ttcttacaac ccgcttgtaa gtgatgtggt    8823
ggtggtaatg atccatgatt ttgatgatga cgatgatgat gaaaatgaag ttttttgtctc  8883 agtttgggta ggtggtatt ctggatgcct cctatggacc ctggagatgt tcatcctata    8943
cagaaatcca atccttaaa tctacttggc tcattgtttt agaattctaa ttccatagtc     9003
tgaaaatttt aataatgata ttaccaataa tattagaaac ttattaagta cctataattg    9063
```

-continued

```
ctatacaaaa aatttaaaag aacccaaaat tccaagcaag actgaaaatt ttttgtctct    9123
cctctgaact atttagaggg acaaattagt ttgttcttat aatatctact ttaaataaat    9183
gtgccatctt taataagata gtagacttct ttgtttggta atgttctatt ttttggagat    9243
cctatgagtt acacttggga aaattataaa agttcactta aagttaataa aatccattaa    9303
gtaatgttca gaactagaca tttccaaatg agcccttgaa aagctcaggt gggttctttt    9363
tgagagttcc ccaaatgttg tcaaccccag gaggaatgga agacctctgc agttttgtta    9423
ttcagattct catctccttc tcagaagccg tagaactggc cgggccctaa ggtccacgct    9483
ccttggttcc agttctgtct tccatccttc ggtcccgggc tcattctgcc tgttcctaaa    9543
cggtggcaag ttaggggccc cagcagccaa cttgtgctta cctggcacta cttcctgggc    9603
agttttcttg gctccttgac ttgttgggcg gcttgggatt tcttttatgg ccctgaaagc    9663
aaaagacaat gttctctttt agtttcctgc aattaaatga tgttagaaat agtcatcttc    9723
acattggcgt acttcctctt tcttctgtag gtcttttaga attttgagtc cattctcata    9783
ttttcttgtt tcatttgctt tattttctaa tacatagaag tttaaactcc ctttaaagag    9843
tttttggcct cttttacccct attaagcttt cttttttctt ttctgtttta gttgttccat    9903
ctgtgtattc tcagatattt ttcttcacc ttttctggtt tatttcttta ttgacctgtc     9963
tcatctgtta ttttaatgaa atttggaaca gggctaaaca gagttcctac ctcagccagt   10023
ataagaatat accgtaataa ctcagagtgg tattaactag attaaaagtt tcaaaaagtg   10083
atgtttttct tgtctctgag gatagaaact tcaacaaaat aaagaagaaa ttttcaatta   10143
gtagaatttc tttgaaagtt tgttcattca ttcatttggc taccttattc caaattgagt   10203
cattcattga gggcttagac tatataaagt gtggttttgt tttcccagca gttcatgcaa   10263
cagcattgca cctagcagct gggaagtctt atagcatgaa taggtgagat tctaatacca   10323
gaatctcctg catgtgtaaa ctaacagtgt agtcttgact gttgtctccc agtaaacttg   10383
gtttcaggag ttttagatcc atgtgaacgt gtacaaggca tttttgctaa ctgtaacttc   10443
ccacttaatc aacaaaaaca aaacactca tttctgaaca ttcagtgcat tcatgattaa    10503
tcttaattac accacaaagg tattttttcaa tggtgatttt gcgggagtgg ggtaacagtt   10563
tcgaaagcaa cattgtcaga aacatagttg attttaaagg ttctttctgg tgactttgac   10623
ttctgctttt ttagaagacc ttacacagag ttgtatttat ttctcctgga atatttcaag   10683
caattcagag tgaaagggta tacattccaa tttgcgtatg agataaaatt tagttacatt   10743
gagaagctat tttctttagt tacagggaaa aaattgtagg gcttttggaa gcctctttga   10803
tttctaatag gaggaatccc tgagcactgg tccaaacaga aatcatctct tcttcattgc   10863
tgtatttccc tcaagctctt agcaaagtgc atggcacgtg aaagcccgga gaagctgttg   10923
gttgaaagaa tggatggtgg tgggcaggaa gcatcaggga catggtttgc ttcagtctat   10983
tggctgggag aaaggccatt taggaaggga tccttagatg ccactggaag aatgtgggaa   11043
gtttgtgaat ctctctttct caggaacaaa agtagaaaaa ggactccaca cagcattcca   11103
agtacagtcg gccctcatta ttcatggatt ctgtatttgc aaattcgctg acttactgac   11163
gtttatttgt aaccttcgag tcaacactca cggtgctttc tcagtccttt gcagacgtgt   11223
ggaatggcaa aaaatttga gttatatgac gtatatgttc ccagctgagg ctgagcaagg   11283
ctcacttctc cttgcagccc tcagactata acaagtgtc cctcttgcta tctacttcgt    11343
gttatgattt tgcattttc ataatccctg ttgatgattt tgctgtttaa aatggcccct    11403
aagcatggtc ctgaagtact gtctagggat tctaagacaa ggctctgacg tgtcttaaga   11463
```

-continued

```
gaaaatacgt gtttgataag ctttattcag gcatgagtta caatgctgtt ggccatgagt    11523
tcaatgatgg tgaatcaaca ggatatatta aatacagtgt ttttgaacag aaaaacatat    11583
aaaacaaggt tatgtattaa tgagttggca aaaatgctgt gaccaaaggc tcccaggaac    11643
ctaccctatt ttcccctcaa tgcaatggtt cagtatttgc taattcagtg tttgaggtga    11703
ctttatagaa catgagtacc atgaataatg agaatcgatt ctgtataata gagtgatgaa    11763
agcacaggtc tgggagccag cagctatatt tctattctgg cgtgactcct gtgtagttgt    11823
catcactggc aaattgctta actgtgtgcc tcagtttcct aatctgtaaa agctacatcg    11883
tttggatgat gtgaggatta aacaaattca tagatgtcta gggcttataa cattcctggc    11943
acataacaag tcattatttt ttattactac ttcggaaggg aattgagtac tatccctga    12003 agaaggtgag tatgggaatt ctctacgggt ctggaatgtc cctatatttg tttattttgc    12063
cttcaagtga ctaactttaa taccctattg tgattagaag ttaaacttct gcaaccaaaa    12123
ggaagcagga agctagtatt tcttgaagtg cttattacat gccaggtact gtgctacaaa    12183
aacaaaacaa acaactgta aaaaaaactt caaatttggc tgcgtgcagc tgctcatgcc    12243
tgtcatccca gcactttgag gaactgaagg gaggattgct tgagtccagg agttccagac    12303
cagcctgggc aacacagtga gaccctgtct ctacaaaaaa acaaaaacaa aaacaaaggc    12363
actccaaatc agtaaaaatt aatcaatcaa taaaaagagt gagggcatt aagtattgtg     12423 gactgaagca atcccagaga gggaattaat tgaagctgag gtaagcagct tatggagaag    12483
ctatgatgta cagagggcaa ggaaggaatt tttctgtaat ttggaaaaat gggaactgtg    12543
agaaagaagg agttggaagc tcatacttag ggagcatcta caaggacgtc tttttcacgt    12603
tggttggaat atccaaatca aggattattt cagaatcacc cagatgatta aaaaactact    12663
gagatccagg ttgtatttca gcagttctga caattgctct gggtcgaagc ttgaatcagt    12723
agttaagaaa acaacaaac aaaacaaatt ttggggcttt tctcactgat ttacagttaa     12783
agctcattta ctcttcctat gactttagat ggaggatatt tccaagtctt caggatggag    12843
acatggaggg aagtgagact agtgatgtgc ctcaaggttt tgctgttgtt ctaaccatga    12903
ggagcactat tcaaacccag gtctgctaga tttccaagtc ttcatttcct tgggcctctt    12963
ggatttcaga agcagagggt aaaggagtg ctggggagaa agatcacagt agctttcaat     13023
tctactcctc agctttccaa aataagtttc aagactggcc gttgcatttg atatggaata    13083
aatacaaaga aggtagattg aagggtatga agatgcagat ttttgatacc agatatgaag    13143
ataacattag gaagcaatct aaaacatgga cacaaacaca cacctgtgcc agttagcctg    13203
tataattcga tttttgttaa gtgtttagat aactgaaggt aatttaagcc ctcatatctt    13263
cccttcatag ggttcttttt ccctctggtt catcagagag ttgccaccaa ttcaggctgt    13323
tagtggtaca cataacctct agcattgttg atacagctat aaaatcccaa atatcagtac    13383
aattgttgat tgcataaaat ttccagttgc atggttggaa agtcctgtaa gtttgaatcc    13443
ttaaaccagt cttaaatgtg gaggaggact caattaaagc tctcctcgtg tcctccctct    13503
gacgtatttg caaaatcctt tccacaaata gaatactgtt tttaatgctt ccccagtcca    13563
attttgcgtt gtagaagacg aatttatgga tgagggaagt ggcattcagg cactccagct    13623
tggtatagaa gcccatggtg tctggtcctc agtcctcaag cccgctcatt tcctcatgtg    13683
aactcagaat aagcagctga aagcaagtct tcaaaatctc agagatatgt ataaatgcaa    13743
gtgtttgggt gagaagtgaa catgggtctc ctctagtgcc cacactactt gactaacagg    13803
```

```
ttttgggctc cacacaatga gggattatca acccctgtcc cagggctctc tgggtcttgg    13863
ttctttgttt ttgatgctca gcaattgtga tcagtgaaac caatgttgct tttctatcaa    13923
gagtccaacc cttttctaag aagggttgtg tttgatatta gggaatagct agcaaagtta    13983
tcaagtaact tgtagaaaca ttcttttgca agagttctta tactgaatga ctgtagttga    14043
cagcagtgca gtactggtca ttttctagga catcttaaaa acactgatga gaagtttcct    14103
ctcagatgtc tgtcatgtca ttcttgcctt tctctacaca gggtcagttt tctcttattg    14163
ctgttaggag ttcctcattg gttttttcagc ttttgggctt tcaaactcta attaatcata    14223
agctactaga gtgtactacc taaagtgtgt atatacacat atatacacac acacacacac    14283
atatatatac ctggtataca tatatatata taatatacat atatcatata tactccccaa    14343
cctgatctgg ttcttcctct gcataaaaga cctcaggcca gtcagagaaa acatgtatgt    14403
tccatggtgt ggcaatcaag cccttgtatt tggttccaat cagtctccta actattactc    14463
caagaagctc ttgttgaaag agccatgttt aaatggcatg ttcctacttt cttcttcata    14523
gtgatcttca tctgtaccat gtacccttct ttcttcttgt tccatctctg ttaggctgat    14583
tctacccaga agtcaaggtt cagctcaaat gctatcccta tcaggtgaat tttccacctg    14643
gcatttgttc ggtgtgcatt gtgtgcatac agcaccttt cccggtacct ttactgtaat    14703
caccagataa ttccttttcat tttagttgta aatagagttg tcttcccct ctatggaata    14763
gatttttatta atgtatagag cagcagtccc cagcctctgg accatggact cgtactggtt    14823
tggggcctgt taggaactgg gccgcacagc aggaggtgag cagtgggcat gcaagtgatg    14883
cttcatctgt atttacagct gctccccatc gcttgcatta tgcctgagct ccgcctcctg    14943
tcagatcagc ggtagcatta gattttcata ggaatgcaaa ccctactgtg aactgtgtat    15003
gtgagggatc tgggttcttc ttatgagaat ctaattcctg atgatctgtc attgtgtccc    15063
atcaccccca gatgggactg tctagttgca ggaaaacaag ttcagggctc tcactgaatc    15123
tacattatgg tgagttgcat aattatttca ttatatgtta cagtataata ctaatagaaa    15183
taaagtgcgc aataaatgtg atgcactgga atcatcccaa aaccatcccc agttccatct    15243
gtggaaaaat tgtcttccat gaaaccggtc atggaactgg tgccaaaaat gttggggacc    15303
actcttataa ggcatattag agtaatttca tagatttcct aattcattta tcatattcat    15363
tcactcagca agcattactg gatgttgatc atgtactggc tttggtggta ggtgcagaga    15423
ttgggaacat tgtcatcaag gagtttatgg ttgagtgagg gagatgacaa gtggatagac    15483
aatgaaaaaa cagtagaata agaactgtga tagaaaagag acagccagga gcattgagga    15543
gaggcactta accagatgga ggatcttggt ccattgatat ggaggtcaaa atggtttaat    15603
agagcaagtg acccttttcaa ctgaattttt taagaatgag gatttagcca gacaaagaag    15663
ggcaggtgag gttgtgaaga ggaactgagt ggtactcttc agagctccag cccagttcct    15723
tggacagaat aaatgcttac taacttatag agctgaatat tgaattaata aaataagggt    15783
aaactgttaa gaatcagaga aataacttaa agaacactga tagctagtgt ttttttgaaca    15843
ccatgtaccc aggtgccttg ccgaaaacct taatgatcat cttgtttaaa ccttacattt    15903
ctcataagag gctggtacta ttgttattct cattttatgg gacgtagaaa ctaagacttg    15963
gagagggaa gtgacttgcc caaggtcata caaccagtac tggagaatta gggattctag    16023
atctagaatt tggactctgg agcttaaggt tttaacccac gacattatgc agagaaattg    16083
acaggatttt tctgttgctg atcaatttac ttggcagtta gtttgttact tccttgtctt    16143
tatttttagtt gtgacaatgc tttcatctta gactgtgtcc cgaggctgct gcttttattt    16203
```

-continued

```
ttatgggaaa tggctatttt tatgatcctt gctaaaagca tgtttaaaca attttccatt    16263
aagtaggggg atgttttttcc ttctaatatc agaagccaat aaatgaaatt ctacaaagac   16323
ttgctggtag caaccttagg aatttctttg catgtgaaac ccatctgaga acttaaaatc    16383
tgggtaaaat tgtagtgtaa tttggtgcaa tcgtctcttt gcacaaataa catcataaaa    16443
tcatagtatt gtcatctagg aggggcctta gacatgatgg aatcctacct tttatatttt    16503
ccaggtgaag aaatcaaagt ctagaaaggt gaaggaactt cccccaaagt ttcccagctg    16563
gtagagacag aaccagggct aggtcctcta ttctgactcc tgaccactac ctcacaccta    16623
atagatggag gcatgcccag ttcctgttca ccgagggcat cagaccatgc catactcatt    16683
gctactgttc cagcatttat agtagaagct caagcaagca ggatgacaga atacctaatt    16743
ctggtcacta caacattata atgatggcta aagtgaatgc cccagccatg cttgtctaga    16803
caggccatct gtttaattgg tatatggttc acgtgagaat ttttaacctc tgtttgtcga    16863
gtcggtgtta gttctctagt gatgaattat ttcctatact tccatttaga ttatttactc    16923 ttaattttaat aaccatacat tgtttacttt ggtattgaag attcccttgt ttttcttctt   16983
tttttctgtt tccagggctt aaaggttagg agtgaccttg ccagacttcc ctggagactt    17043
acactgtctc ctttcagatt tctgaagcag ttgggtgcta ttttttagtcc actatcacca   17103 atgtgaaaat ggaacttgca ttatttcatt atagatattt cactttagta ttgacagaat    17163
taaaaaaata atttgatctg tgcttgatct agcagccagg ttacaataga catttttagt    17223
tacctggtcc acatgttgaa aaacatgtgt cttctctgag actaatgact aagcccgatg    17283
ttggttatat actgtttact attaaatttt ccccttgtag tttaatattg ttccaggaaa    17343
tgaaatgaaa gtttaataag aatggcaatt gatggaccca tatgtcggaa gtataactaa    17403
tgtccccgtt acatgtgtta aagaaaggca tggctggtgg gttgtaactg tactacacca    17463
agatgatttg acacaactta ttctacagag atatatattt atcaggatag aatttataac    17523
taaacaaaac tatagcattt tttcactttg attttttttta aatgagtcaa agaactgcta    17583
gaattgtcag ttaaaaaatt ttaaaaggag atatgaaaaa atcttacaat tcacaatgct    17643
gtaaagagat aatgtaggga ttaatatgtt cttgatatca atattttatg acttttatac    17703
atgtagaagc aaaacaattt gaggtaggtg aagttagtat ggacttcttg agattgtcct    17763
tcacatttct tttcctttcg gtgaaaaatt gaaggccaaa atgtattttc ttctggtttt    17823
gaaaatactg tcaagatcct tgcaacaaaa tgagttcctc taaggagctg aaaacaaagc    17883
tcactcccct cgtgatactc tgagaggctt tgctcagcat cctgcattct ggtgattcct    17943
tggagacaga tgatgctaaa cacaggaaga ttaggtcaat ggtaactttt tctaagtcaa    18003
tatttcttct ccttgggaga tgatcatttt aaatcttccc gaagtccagg ctaaaccttt    18063
ctaattgaat ctccatgaag gagagctcca gcaggtggag aggaagtgag aaagagaaat    18123
gaaagctgca cgcctcatga cgctgtgcca gggagttctt aaaggtgagg gagtttctttt   18183 ttggtaacct aagctatgtg aatcagaagg ttcattagct tgtttctttt tcttttttgt    18243
aaactcctac ataattttag taaacaggaa cagtaaccta atgtgatatc ccactggccc    18303
aagacttagt gcatcttcaa agttgcttaa ttatgtccga aacagacttt tgtctcttga    18363
tgagaaaagc atggttaaac gtgtgatgat ttcctattgt cctgagctca gatctgtaat    18423
tgtggccaga ttcatgcatc tctgctgcct tctcttagaa gaatcatatg taggcttgtc    18483
agataaaaca ggatgcccag gtaaactgga atttcagtta aataacaaat aacattttag    18543
```

```
catgtcccat gcaatattat actaaaatat tatttgttgt ttatctgaaa ttcaaattta   18603
attgaatgtc ctgtatttt gttggttaca tctggcagcc ctagccatgc tgcctttctg   18663
cttaatgggc ttaattttt gaaggctgga ggttttctgt tatggtgccc gtttccacct   18723
gcttttctac caggaaagga ggcatgctga tgtagaattt gcatccttat ttttgtcatt   18783
attattgatt ataacagatg acataggttt agattaaacc tacaatgaca ttgctgtcat   18843
tcagataatt gtaattattg ctaattgtaa agaaggataa ttttttttga aatgactatt   18903
atttgttttt tgttttgtt tttgtttttc ttttttcta attatacttt aaattctagg   18963
gtacatgtgc acaatgtgca ggtttgttac atatgtatac atgtgccatg ttggtgtgct   19023
gcacctatta actcatcctt tacattaggt atatctccta atgctatccc tccccctac   19083 ccccaccca cgacaggtcc cggagtgtga tgttccccac cctgtgtcca actgttctca   19143
ttgttcaatt cccacctatg agtgagaaca tgcggtgttt ggttttttgt ccttgggata   19203
gtttgctgag aatgatggtt tccagcttca tccatgtccc tacaaagaac atgaactcat   19263 cctttttat ggctgcatag tattccatgg tgtatatgtg ccacatttc ttaatccagt   19323 ctatcattga tggatgtttg ggttggttcc aagtctttgt tattgtgtat agtgccacaa   19383
taaacataca tgtgcatgtg tctttatagc agcatgattt ataatccttt gggtatatac   19443
ccagtaatgg gatggctggg tcaaatggta tttctagttc tagatccctg aggaatcgcc   19503
acactgactt ccacaatggt tgaactagtt tacagtccca ccaacagtgt aaaagtgttc   19563
ctgtttctcc acatcctctc cagcaccgtg tgtttcctga cttttaatg attgccattc   19623 taactggtgt gagatgatat ctcattgtgg ttttgatttg catttctctg atggccagtg   19683
atgatgagca ttttttcatg tgtctgttgg ctgcataaat gtcttctttt cagaagtgtc   19743
tgttcatatc cttcgcccac ttgttgatgg ggttgttgtt tttttcttg taaatttgtt   19803 tgagttcttt gtagattctg gatattagcc ctttatcaga tgagtagatt gcaaaaattt   19863
tctcccattt tgtaggttgc ctgttcactc tgacggtagt ttcttttgct gtgcagaagc   19923 tcttcgttt aattagatcc catttgtcaa ttttggcttt tgttgccatt gcttttggtg   19983 cttggacat gaagtccttg cccataccta tgtcctgaat ggtattgcct gggttttctt   20043
ctaggttttt tatggtttta ggtctaacat ttaagaagaa ggatacttaa agtataaggg   20103
aaaatgttac aatgtatgaa gggaacatga agaaatagaa tctggtaaaa aagagttctt   20163
gcttttggga ggccaaggcc tcctggctaa catgatgaaa cctcatctct actaaaaata   20223
caaaaaatta gccgggcgtg gtggcacacg cctgcagtcc cagctgcttg ggaggctgag   20283
gcaggagaac cacttgaacc caggaggtgt aggttgcagt gagccaagct tgcaccactg   20343
cactccaggc tgggcaacag agcgagactc catctcaaaa aaaaaagaa aaaaagagt   20403 tcttgctttc aaaactatgg attaggtaac ttttgtgaat gagtaagatc atgagtatta   20463
taaaaatagc acctttcttt tttgtcttgg ggaaattatc ttatttttta attggatttc   20523 agaaagagt atttcagaga aataaatctc tgaaatgctt tttgaagtgt gaaagattta   20583
gaagacaaaa gcaaacctcc tgtctagata aacattaaag agatctgccc tcccctcctc   20643
tacctattca ggttgcaaca ctttggggt ggctgccttg gtagagcttg atcgtgactc   20703
tggtggcttg ggagatggca tgctgcacaa gggattcatg gttacagcgg gcttgtggga   20763
ctggggctct ccaatacgtg gttgggtttg taaagaaatc agagctatgg tgtgaacaaa   20823
aggatatgca tggagacag tgagacaagg aaatgctcca gaaattattg gaatataggt   20883
cagataacta actgtacttg tgccattttc tgggggaaaa ttctctgaag gcttttgggg   20943
```

```
aaaagaatgg aagtgagaat tctcaggtcc tcaaaatatt tccttttact cagtcctaac   21003
ctgaggccgt taagaattc ccagagtcac gatggaaggc atgtttggga gtaagagcca   21063
gagtgagggt tagaaatgtg ttgttggcca ggtatggtgg atcatgcctg taatcccagc   21123
actttgggag gccaaggcag gtggaccacc tgaggtcagg agtttgagac cagcctggcc   21183
aaaatggaga aacctcgtct ctaccaaaaa tacaaaaatt agccaagtgt ggtgacacgt   21243
gcctgtaatc gagctcttcg ggaggctgag acaggagaat cacttggacc caggaggtgg   21303
aggttgcagt gagccaagat catgccactg cactccagcc tgggtggcag agcaagactc   21363
catctcaaaa aaaaaaaaa aaaaaagaa agaaatgtgt tttccagggt tctgggtact   21423
taggaatttg gttgcttttg caggtggaag tggaggtgac taggtaacag ctgagtgatt   21483
ttgccccagt tggacatgag ccaggttgag cagaaagccc tgggatgcgg ggaggggggt   21543
ggcggggaag gaattgaaag ttggttgtgt ggtttggctt tggcttcatg gcatgctcac   21603
accttgcttc gcatagcatg cttagactac agcaggagca tcaggaagtg gatttctgag   21663
ctcaatacaa aaagttataa ataccaccta taagggcaat aaagatatat agttgatttt   21723
cttctttgca aggccaaatc ttataggaac ataagagcga atgagttaca gcctgggaat   21783
ttgagcctta tattcagaga ttttaggttg cttctgattc cgctgtctag acaaaaccat   21843
gagaggatag tgtctagaaa tgagaggaag ctcttccaat gcagaggcta gaatgtgtca   21903
gcctgtgctg cgaggcctgg gatagatgtt tctgaaaagt aaaagggcag ctttcctact   21963
ggatacttga tcctcaggct ctagaaaact ctgctttatt aactttgttg acttcctagg   22023
caccacatgg gatccttgtt cttcctcctt gtaagcagta attgaaatca gtttggcagc   22083
ctggtttaca gtgaccatgg tggcttgtct cccgtgctct tacctcactc tgttgatgtt   22143
gtaaaacctc cagctaactt catggggtgg ctgacccacg ttgctcattt attcattcaa   22203
cacatattca ttgaccatct actctatgcc aggtattgtt atcagcactg gaatagatcc   22263
agtgaactat tgatctattt gtctaatggg acaaattgac aaattgggaa agattccatt   22323
acacaggtga catttaagca aagtcttgaa taagggaggg aatagtacca tgagatatcc   22383
tggtgaaaag caatttaggc tgagggcaca gcagggaaga ggccctgatg tgggaacatc   22443
cctggtgtct tgaggtacag aggccagcat ggctggcacg gagtaagaag ttggaggtgc   22503
cgggcatggt gactcacacc tgtaatccca gcactttggg tggctgaggc agatgggtca   22563
cctgagccca ggagcttgag accagcctgg gcaacatggt gagacccat ctctacaaaa   22623 aaatacaaag aaaattagcc agatgtggta gcatgcatct gtagtcccaa ttgcttggga   22683
ggctgagatg ggaggatcaa attacttggg aggctgagat gggaggatca cttgagtcca   22743
ggaggtggag gttgcagtga gctgagatca tgtcagggtg acagagcgag accctgtctc   22803
aaaaaaaaaa aaaagaaaa agaaaaaaga aaaaaaaga agttggaggt gagtaaggag   22863
aggaacgtgg gggacagagt cctcaggact ctggctttta ctctgagtga gtcgaaaatc   22923
caattaaagg tttgaaagag aggaatgacc tgatctgaca ttttattgtg aacgttttca   22983
aatctttaca gaagtggaag agcataacga tccttcatgt acacatcgcc cagcttcaac   23043
tatgatgttt catttgtaaa tatttccgtc tacacttcca aaggatgatg actattttta   23103
aaagtccaac tataatacca ttatatttta aaagttaaaa cactatgtct ttaaatatca   23163
agagtttgta ttgattcgca ctttgaaggt cgagctgatg aaatttcctg aggggttgga   23223
tgtgacatga gagaggagtc aagtattgca tggtaattaa aaacctttgc agcatagtcc   23283
```

```
atttaccgaa agactatatg tatgcacttc aaagcaggtt ttaaagatta acatcaagca    23343
tctggcttca tgagttttaa cttcttttca taaatgttat acaatgtcat catctctcca    23403
gctagagaaa atgctattat tcttattttc aaatgaggaa aatgacgcag aattatttac    23463
atattatgta acttggtccc aagtcccttc gatactggtt tagaaaatcc tagtaaactg    23523
gaagtgactt atccaaaatt aaaatttatt ttgctctatt gtcttttgtt gcctatggga    23583
actttgtgca ggtaactagg cacatgtcag gactgattta ctgacctctc aaggtatctt    23643
taattatttt gggggatatc acggaatgag ttctacacaa ttcatttgaa tcgaattgaa    23703
cttaagaaaa ttcaaatgat gcattggctg cctcctattt attacatgct gctcataggc    23763
ataacagcat agtctaacaa gtataaaacc tgtgtaactg tagctttcag tgcagtgtga    23823
tgagggctga aagatagtg gtacaaagaa gagaggtagc agagtgaagc tgagtcaata    23883
tgatgaagat ttctctagac ttgaaagggc tagaaaaggt tattcttggc aggaaaaaaa    23943
catgagccaa ggcataagga taagcacagg catggcagat ttgggaatgt catgtaattt    24003
gttgctgggc tgcaaagtac atggaagggg agtgaaggaa cagaaggaga tgaatctgga    24063
gggagaggtt aaagtgttcc agagagcaat atgtaggtgt tactctaagt caaagaggtc    24123
gtaatagcat gtccagactc caaaactcta aacaagtcat agaattgctg ccttggtagg    24183
gcatatcaca cacatcaacc caatcctctg tcaccatgac atccatataa ctgcaactct    24243
atacatttcc cagcctatgt tcccagagtc tccagatgac attgtctgca aactgcactg    24303
cagaaggctc tgctatgtct tcttaaaagt aagcaagact gttttccttt gttacatgag    24363
cagcaaaagg ataggtgct ctttgacctc acttactgta gggtggatag aaagtcaag    24423 gaagagtaac ccagaagatt tagttttaac tttcgcatca aagaggtccc ttagcatctg    24483
ctcagagatg tcacaatttc tggtgtgtga ttatgtttaa gaattcggcc ttgccactgt    24543
tgaagttgtt ctgtggaaaa agaacctctc ttaattttac atgatgccca acttctcttt    24603
tattccagaa tcactcatat gctgttggac tctttccagc catgtgtgct aacctaggca    24663
atgtcataat agatgaatta tgtttacttt gtctttgata tctcagctct tttatcttct    24723
attcaagttc ccacctccat cattactgat agtgttcgtt gaacaaagaa tatgtcagat    24783
atacagaagt gtttctcccc ttttctctgt ctctcttttc cttcctttcc tttagtttcc    24843
tttctctgtc tgttttctga tgcctcattt tagaaaagtg attttttttg tgggaaaatc    24903
attttagcat tagaaacgca atggctatca ctgacagctt cctctgatga aacggccatt    24963
tgtcatcatt acacggtcat gggagtgcta agaagactta aatgcagggc taccacccct    25023
tcccaattca tcttttatcc atttatttc tctaaggaaa gggtttgaaa atgggctt    25083 gccctcttgg atgcagtgaa gaaattctag ctggctacag atgttattgt tggtcggagg    25143
caagggataa aatcatggtc acaccattgt agcgccagat ggggaatgta gcaaacatag    25203
ttgtaatttc tcatttaca gatgaagaaa ctgaggtgca gaggggttcg gtgacttgtt    25263
taaggcatgt aattgttatt ggcagctttc tgttcagaac ttaagagtat gagtcagtct    25323
agatcttttc atcacaatac tctgctcctc ttacttttc ctgaaatttg tcacattgac    25383
agcaatgtga tccctaatga cacacagatt cccaaataat ttttgtagta aaaatttcca    25443
tttgcaattc tggacatgtg tgtgtgtgga attttatgtg atgacatatt ggtcctatct    25503
tttgaatagg atcataaatg aaatgactta tggatcacat tcaaaagcag gccagggggcc    25563 aatgtgtaag caggtgggtt ttcatatttg gagttctgta cttttgtgtt agtcagtggg    25623
tctaggactc ttgtagtgta tttcccaagg gccaaagtct tctgccttga ggtgtcagct    25683
```

-continued

```
ttccaaggca gaggctggat gctttctctt ccttctgggc tcctttctct taggcttccc    25743
ccttctcttc tcctccattt gtatctgtcc tttttctcgg tactttccct ggctggtctc    25803
agctagatgc tcactcaatg ctgttgaata aatgaatgaa tttcgtagta attctgcagg    25863
taaatcaagt tattgtctcc caatacggtg ctatgctttc tgaggaaatt agactggaag    25923
tcaggctttt taaaaagaa gatgtggtgt caaattgcag ctctctctct ctctcgactt     25983
accttttttc tatcatccat atgccttctt tcttgtatct ttgggttccc agacctcacc    26043
attcattagc acttggaatg gattggtaag aataaagaaa ggagaggtgg tgaaactcag    26103
cttgggtcat ctggttacac attagtaact gacaaaagat aaaagatac agactaaatg     26163 ggttttagg gaactttttc cagtctattc ttgtttccca ttagtgtgaa aaatcaacac     26223
ttgcttgtat tttggggtga agacattttt cttaagtgag tgggaaagcc tcttgacatt    26283
ttaccgagag cctaaatttt tgaatggtga atgctaatgt tctttgtgca taaagaattt    26343
cagaacttgt atatatgagc attaatgatg catcattttc tatttgtgag ttaaactagg    26403
tattatctgt aatcatattt ttaggaaaca ttcaaacttt catcaagtca ttctcttata    26463
tgactctcag ctccattaac tctgttttca tggaactcaa cagagttctt aacgtttgca    26523
ttataaatta aattagcatt tccoctcaaa gaagtattgc tgtccttaca ataaataatt    26583
gtagacaatt tcttttcttt tcttttttt tttttgaga caggttctct ctctgtcacc      26643
catgctggag tgcagtggca cagtcacagc tcactgcagc cttgacctcc tgggctcaag    26703
caatcttccc acctcaacct cctgagtagc tagaattata ggtgcacacc agacctggct    26763
aatgtttaaa ttttttgtag agttgggtc ttgctatgtt gcccaggctg gtctctaact     26823
cttgggctga agcattcctc ccaccgcagc cttccagagc agtgagatta caggtgtgag    26883
ctaccatgcc cagctaattg caggtgattt ctaatgggat ttagtatttc tgggtttaag    26943
gatgagatct gaggtaatga ctttgtttcc agatgtgaaa taatttgctc ttgggttgtg    27003 agcccttttgg gtgggctccc aaggatcctg ctctcttcca ggagcccagg ctctggggtc    27063
agactgcctg ggtccttgac tccctgtttt ctgattgtac aactttggtg agtggcctaa    27123
ttcctctgtg ccttggctac cttggttact atttctaaaa caactggtgt gtagtagta     27183 ctgcttagag tactttcaag ggttaaatga attaatccat gtaaaacgct taaaatagtg    27243
cctgccacaa ccatcaattt agtgtgaaaa tctgctcacc tgcttggcca gccccttttca   27303 ctttattaaa ccaagggtcg tgctgggttt tccagaagtc taagttgcgg tctaatcttt    27363
gtgcagaagc tgaaatagca gccataacgt tctccctaga tgatttcgtg gagcttcttt    27423
gaactgtatc tatctccagt cattttttgtg gaagaaattt tcttctgtac tttttaggga   27483
tgagaattac ctgccttggt ttattaacta aaagacacca tgattacaaa taaaattaaa   27543
taaatattgt atcactaaat agataatatg agatagatgt attaagtttt cagataaaca    27603
gtataaaaga gctagagtaa tttgtaaaaa gttgggagga cctattttgt catgcaggaa    27663
acaattttta acttgcctac cccagaacat agctaccaca tggttagggt ttgcccaaac    27723
ctggcccagg agtcatttac cttgagcttt cctaaaaagg aggatcagga ttttcctctc    27783
cagactctat cattttaggt agagtccttc ttgtcaattc tttttaagaa catacattta    27843
cttttgtgga aaataaatag atacaaaata aatacataca aaattgcata gcaattagaa    27903
atacccagga ggtatgttat ggtcacagac acaaactgcc tccaacttct gtccatccat    27963
agtgatattt aaagcagaga gaggtacaca ggtaaccaca tttagatgga ctgggatgtt    28023
```

```
gccacacata caagcattga taactggctt ctcattacct gaatacattc ttctgtcaga    28083
gcaacagact cagctatgct tctggcaaaa ttgttcttaa ttctctattg attaatttat    28143
tcggtaagta tttattgggt attttctgtc tgaaaagtgc gattccaggt gctttatgtg    28203
tctctgtgtg tgggtgttat ataaatactt ataatactgt atccatactc ttgaaaagct    28263
tagttgggaa ggcaaggcat gcaataagga acacagaatt ttagtcattc cacaaccatc    28323
tgttgaatgg ctgctattgt tagtatcgtg gtggaaactg agaagcaaag atgactataa    28383
taggatctct tttctggaga tgcacagtgg acacgtagtt atatgatgat gataaggact    28443
ccagaatagt tctatacatg atgctctggg gccacatgca gattctgatg agaaacaatt    28503
aactcttttt ggctgctacc tgagaagggg taattgtcac tcaggaggtt tttgccttt    28563 gaccaacata gaaaggagtg tgagtgaagg ctagaggtgt actaacttgg tcagggcagg    28623
gtgacacata aaattaacca tcacagggaa gggtagggct ggagaggcag actgtggcca    28683
ggttacaatg cgctgaggct aaggagactg tgtttatcct gtaggccagt gggtcttact    28743
ctgaagtctt ttgggtggga cattcatgga cttcaagaga cctgtgaatg ccctaagatt    28803
ataagtaaaa tctgtgagtc tgtaactaaa gctaaagcta tttttctggg gcccaccatc    28863
taaagaagat tctgaagcct tagggtagcc gtggaggaga catgaaggtc cattttgcat    28923
ggtagaaccc tgcctggctc ttgctgcagt gtgggaggac aggtttgcaa tgtgaggtg    28983 tggcaggcat ggatttggga ggattggcag aggactcacc atgtccatac actcactgag    29043
atggcaaata tttattaatc atccaactgt gtatcagaca ctaagaataa gctgggaggc    29103
catggcaagt gaggtcacca cagtccctgc cacagtggag gttatggtat acaggtaagg    29163
cagggaagag cactgcaaag ggtttgccca ttgcatcagt catttattta tgcacatgtt    29223
gattcaacaa ttatttctat gccaagctgt cttcaaggtg ctggaggaaa tgaagcgtac    29283
atttcactgg ggaagacaga caataagtaa acacattaaa atctggcttg gcttgatgtt    29343 ggggagggt gagtgccata gagaaaacaa accatttatg cagccaacaa acatatgaaa    29403
aaaatctcat catcactggc cattagagaa atgcaaatca aaaccacaat gatataccat    29463
ctcacgccag ttagaatggt gatcattaaa aagtcaggaa acaacagatg ctggagagga    29523
tgtggagaaa taggaacact tttacactgt tggtgggagt gtaaattagt tcagccattg    29583
tggaagacag tgtgatgatc cctcaaggat ctagaaccag aaataccatt tggcccagca    29643
atcccattac tggctatata cctaaaggat tataaatcat tctactagaa agacacatgc    29703
acacgtatgt ttattgcagc attgttcaca atagcaaaga cttggaacca acccaaatgc    29763
ccatcaatga tagactggat aaagaaaatg tggcacatat acaccatgga atactatgca    29823
gacataaaaa aggatgaagt aatgtccttt gcagggacat gggtgaagct ggaaaccatc    29883
attctcagca aactaacaca ggaacagaaa accacacact gcatgttctc actggtaagt    29943
ggaaattgaa caatgagaac acatggacac agggacggga acattacaca cctgggtct    30003 atcagggggt tggggctaa gggagtgata gcattaggag aaataccaaa tgtagatgac    30063
gggctgatgg gtgcagcaaa ccaccatggc acgtgtatac ctatgtaaca aacttgcaca    30123
ttctgcacat gtatcccaga acttaaagta taattaaaaa aaaagaaaa gaaaacaaac    30183 cagtgtaaga ggatgaaag taataggctc gtttagaatg gtgtgagaaa gccaggcagg    30243
gagaaggcgc tgagacaggg aggtcctgga tgtgtttgtg gaagagctgt ggcagcacct    30303
ggaacttggg gagcaaggga aggagtgtgg gcaggcaagg gtgagggtgc aggggtcat    30363 gctgggcctt ccaggtcacg gaaggacttg agctttactc ttgttgtggt gagaagctgc    30423
```

```
tgagggcttg gagttagggg agtgaaaaga tctctactat aataqggaga gttcgggatc    30483
tgtaacttaa ccccaggagc cagcaaagct ccctggagga aatgcagttt aagctgagaa    30543
tgggaggata aacaggtgtt tttcagagaa gaggaaggt gctctaggca cagagaacaa     30603
catgctggaa tgcttctact agatcatagg ggcaaaatgg gagtgcagga gtaggagagg    30663
gctttctggg aaagatactt atttttaattt tgcatgcatt gagttttga ggtttctttg    30723
gtttgttcat gtggaggtgc agagtgggta tttagcacat aggtctgaag tccaggggag    30783
gggtgtggga cagcagttgg atgtggcaga gattccacaa agagcaaata tcatctgaga    30843
atggcagagg gctgagggca gagccctgag gaacactggt gtttaggagc ctgctggaga    30903
aagaaaatac tgcaaaggga acggaagtgg agtggttgcc agacatagaa gctagtgtct    30963
aactagatgt catgagatgt ggggaaggtg ttacgtatct aagaatgcaa agttgaaccc    31023
ctgtgaactg taatacttaa gataagtcgt ataaattgtc tggaactaga gcttgatttt    31083
ccaggagaga tgaaatgtgt gtaggtgaca ggaaacaatg aatatgtggg cgagtgtagt    31143
gtgagcaatt tctcagaggt gaatttgaca gcattttgct taggaagcta caaagagacc    31203
aatgctagtt ggtgcaagga attcaagaat ttggacttaa gtctatataa tgatgatttt    31263
ttttttttaa cttgagtttc ccggtttatc actcccagaa tataggcaga agtttgagat    31323
ttttatgtgt attttctgga aaagatagtt tcagtgtttt ttacattctc aaacaggttt    31383
atgatccaaa gaaaaggcag tggtcacaga tacatgaaac gacaaggtat tcaaaggaga    31443
acgttgtact ttatgacagt tctttgggca gtggcttgca ggatgagttt gaggaatgat    31503
tggaggcagg agagtaattc tagtaattca aatgtggagt attgttgatc tctcagacac    31563
aaatggaaaa acaaggaatt caaagaaaga taggcagagt gttttgaaga ataattgat     31623
gaaatttggt aatgagttag atgtaggaga tatatttagc aaatatttat taaggactgt    31683
attaatctgt tatcatgctg ctaataaaga cataccaaga ctgggtaaat tataaagaaa    31743
aagagattta atggactcac agtgccacgt ggttggggag gcctcacaat catggcataa    31803
agcaaaggag gaacaaagtc acgtcttaca tggcaataga gtgtgtgcaa gggaactgcc    31863
atttataaaa ccatcagatt tcatgagaaa tattcactat catgagaaca gcacagacaa    31923
aagcctgcca ccatgattta attacctccc actgagttcc cccaggacac atggaattat    31983
ggaagctaca attcaagata agatttaggt ggggatacag ccaaaccata tcaaggacct    32043
actgtatatg gttaaaattg ggagcaaatg agacatgatt cttgccttct tggagtttac    32103
tgtttactag gggaacatac acttgtcaat aatcacccaa atataggatt ggaaattgtg    32163
gtaagtgcca tgaaaaacaa gtatagggaa ttttgagtgt acatagcttt ggggacttga    32223
tttgatgagg gagccttatg aagttattgc actagaactg aattaaacca catttctagg    32283
aagtggacat ctatttgttg gttcttaaa tttagcttta cagaaatatt tccttttaaaa    32343
accaaggctt cttaaatttt taaaactgct tggctaatca ggggaataat gcttttggat    32403
agctggtatc gttatttatg gttggaaaaa caacagtatt tgattacatt gagctttaaa    32463
cttttccttt gattaatgaa aatttttattg gcccatagtt tttattatgc tctgttttta    32523
cttggtccaa gagattctat tctctggacc caatatgaat accttcagac atccctcttt    32583
tttttttttt ttttcaccca ggctggagtg cactggcacg atctaggctc actgcaacct    32643
ctgcctcctg tgttcaagca attctctgcc tcagcctccc gagtagctgg gattacaggc    32703
acctgccacc acacctggct tattttttgta ttttttaccag agatgggqtt tcaccatctc    32763
```

```
ggccaggctg gtcttgaact cctgacctca tgattcaccc accttggtct cctaaagtgc   32823
tgggattaca ggcatgagcc accacaccca gcccagacat ccctcttaat tatgttgaat   32883
atgtaatatc ggtgatttca tttgaaaata tttagtagtc gaactagatc aaggcagtta   32943
agcttcctat ttccatagat gcagtggtat tgtgtctttt ttatatgatc tctcatgctt   33003
ctggacatcc ttttttctgc tattcttcat tccttagcta cacttggtgc ttcgtggttg   33063
taatgcattg tcatagatgc gttcatttct cattcgatct tcagctctat ttctttccag   33123
agaatctcta caggcatctg ttaggttgaa ggacatctaa tgtcttaatg tgtagcttgg   33183
taaaccagtc aactttctat ctgagtctta agagaaagtg tccaagatga gaaacggtac   33243
aggtttggtg acaactcagt gagaaaaaga agaattttac aaggaaggag gtatcttagt   33303
aattttgcta agaagtagg taaaccttca cttataataa agggataggg ctcggttagg   33363
gtttgtgaag tctcccctta ggaaagcaaa ccctgaaata ttttgaatct tttaaagaag   33423
gaaaataaga gtcttttaaa taaatttta aaatttattt tatatatttt ttatagacag   33483
gctctcactc tgtctcccag gctggaatgc agtggtgcaa tcatagctca ctgcagcctt   33543
gaatgcctgg gctcaagcgg tccttctgtc ccagcctcct gagtagctgg gactgcaggc   33603
atgagccaat gtgcccagca agagacattc attttggtac tgtgatggta cagaaaaaca   33663
aagggccttt gaggccgaag gagcagaaga aggatggact tagacatggt ataggcactt   33723
tctactaaag agctgtgaag ctaaaaatgc caggtctatg acaggtgcag tgggccaagg   33783
ccaggtagag agcagcagga agagaggagg tggggacctg tacctaggcc catctgctgg   33843
gactgatcta gccataggta ctcagagaag cccagattgg tgcctgaccc acccttatgg   33903
cccagacatg gacacctccc agtctgttcc ttcctgctgc ccatggatgg gctgtgttag   33963
tctgtattct gaggacacag ctctctgtct agaggaagtt atgttatctt gatctgatgg   34023
atactcaacg tgaacattat ttcaacgtgc cacagggtct tggagcccag aggaagaccg   34083
ctcttgcctt ttagtttata ttctttgttt ttttttaaat aacatttga cagtctttat   34143 ggagtaagtc tgggccaaaa tgataattga caatgttatt tacatggatt tctaagttgg   34203
ctaaaaaagt tcctttatgg ttagtgaata tagcccatgt agtttccccg tcttctttag   34263
atgccttcta tttctatgcc caaagtctgc agttgatttt cagtaagctg ggggtcatct   34323
tagagataaa atgtagatga atggcatttt gctgacagca tacatctttg ctatttctga   34383
ggaaaatggg ctctcgctat taaatctttt gtcaatattt ataaaaatag tatttacata   34443
ttctatctat attgtggaaa ctatacattt attgattcag tcatttgata tcaatgttgt   34503
tgagtcccta ttccaagtga ggcactatgc tctaagcaca tggcatttta aagatgaata   34563
agacaccaag aactttgcag atagtaatgg aaatgagaat taatcaattg aagattaata   34623
tagtaagtag cagaagagaa ataaaaaaat cttctagaga gttcagaaca gggatgttga   34683
ttcaagttta tggggattag gagtggctgg taagggaggc attcaggcaa aagacataaa   34743
aatgcagtat tcccctcgca ctcattagga tggctactat attagaaaaa gaagagagta   34803
agtgttggag aggatataga gcaaatagaa accttgtgcc ttgttcatga gaatgtaaaa   34863
tggtgcagcc actgtggaaa acactggtga ttcctcaaaa aatcaaaata gaattatcat   34923
atgatccagt aattctactt ctgggtatat atctaaaaga attaaaaatc tgggtcttga   34983
agaaatattt gtatactcat agttatagca acattattca taatagccaa aaagtagaag   35043
caatccagat gtctatagat ggatgaatgg gtaaacaaag tctgtgtagt atatacagac   35103
aatggcatat tagtcacatc atggaccttc aggacattat cctaagtgaa atatgctaga   35163
```

-continued

```
cacaaaaagc aaaagtaggg tttcacttaa tgaggtatct agaattgcca cattcacaga    35223
gaacaaaagt agattggtgg ctgctagggg atagggggaag gagaaaatgg ggaattattg   35283
ttgaatgggt atggagtttc agttttgtga atgaaaatg ttctgaagac tggttgcacg     35343
atgatgtgag tatatctaac atgattgaat tgatgaacac ttaagcgtgg ttacgatggt    35403
aaattttgtg ttatatatat cttaccacaa tttaaaaaat atagcatttt attatgtagg    35463
cgtgggtggg aagatacttg acacattgga acttctggcc atgcgtatac tgttcactca    35523
cttattcctt cattcattca acaaacatgt attgaatgct tgctatgtgc tgggcactga    35583
gctagatata acaattaata aggcttataa gacattgaat ctatcaattt catgcttgct    35643
aaatatctac tcccacctcc aaaggcacta agcttctaca gttagatatt catagctgct    35703
tcctactgac ttgaatcatg cataggatat tagtaaacaa gcaataaaaa gatttgaggt    35763
tgatgggggt gggttcaaca gcatggtggt gaaatggaaa gagatgggta acagaatatg    35823
aactagaatt gaaaactgtg agccagtgct ctctaatgaa cattaaaaaa taagaattc     35883 ctatttgagg ctgccaacct cagaactaag ttatttagaa tggacgaaat tggcaaagtc    35943
agacgtactc aacccaagga gccaatattt tgtgaatatt atggcaaatg tagtttgaga    36003
accactacca caaaattgtg aaccataata atgactgaga aggcagggag aggttataca    36063
atttgggcta aaaggaaaga cagggcttgt gaaggggagc gccagtgaaa gtcagtgtgg    36123
ttcgggtatt tgggtgggga ctggaagcag gaagcttgag cttcctttgc caagagaccc    36183
tgctggaagg gctatcatca attgactta gctcatctta ggattttcat tttttaaaaa     36243
atgttcacag gaaccttcac tccatctata ctttcaatgt ctgcctacct ttctttctta    36303
tacaactttg aacactctct ccattcattt aaatatatta tggagtgcca actacatgcc    36363
aggtactgtg ctgggctctt attccaccct tatttgattg cacatgcctg ccaagtcctg    36423
ggccaatata acatctactc ctatgtctgg tctggcgaga gatgcaaact catcttcctc    36483
tactttcctt acctccttcc ttccagtctt cttcaagttg tcttcattga ggcaatttct    36543
tttacctgtg ttttaatcc caactcctct agtttccttc ttggctttat tcttttatct     36603
tcctctttgt gctttcaaac attccctttc tcctggccca tgcccttcag tctacacgag    36663
gccttctcaa gtctcttcat tctaaaaaat tcattttctt gggtcttata ttcttcagct    36723
gccaccctat ctgtatcttt tcctattctc ctccaagttc tcaaaggaat gccttccctc    36783
attttcatct ccttacattc catctgctga attttggctt gtgcctgtac ctgtctaagg    36843
aaactccttg ctaagagtct gctttgtcag gtctgaattc acttaaccag tctttgcttt    36903
gttggacttc tctgccccat ttgccattct tgatcatcct ctccataaac ctttctactt    36963
aaagcatttt acttccttat tttcttggtt ttcctagaat ctccttactg ttcattttca    37023
gcttcctttc tgtgttcctc ttctcttcct acattttttt ttagctttct actttcttaa    37083
agcattttac ttccttattt tcttggtttt cctagaattt tcttactgtt cattttcagt    37143
ttcctttctg tgttcctctg attgtctctc tttctacatt ttttttttct gtgttcctct    37203
gattttcacg cagtctggag ttgtcatgat caatcatagc ctactgcagc ctcgacatcc    37263
taggctcaag tgattctccc acctcagcct tacaagtagc taggactaca gtcacacatc    37323
accattctca gctaattttt ttaagaagca tttttataga gatggagtct tgctatattg    37383
tgcaggctgg gctcaaacta cagggcttaa acaattctcc tgctttggcc tcccaaagtg    37443
ctgggattcc aggcatgaac caccatgctc agtctctaca tgttcctaaa gaggagtttt    37503
```

```
gaatattgaa gaacagtatt ttcaaattac attattcaag ttataaaaac tgatatccag    37563
ggttatgtgg caatgacgta aaaatttgaa ttgttatttt tttgacacat gttctgtgtt    37623
gtccatcagt tcatctgagt tccaaatgtc ccagctgttt tatgctttgt ctctgtttcc    37683
cagagaccct gagtgtggtc tagagttggg atgagcattg gtctctaatg gttctgaaat    37743
aattgtatat tcctgcaaaa acattaagtc tattagaaac cagctaattt cattttgtca    37803
tttttatagg taacatattc tggtgcaggt agtatgtttt taaaacaagt ttgcaataaa    37863
caatttcccc tcaaggttaa tataataggc aacacctttt gctgcaacag acggcaagag    37923
gtaatgaaag attagcttac attatgattc attatttcaa aatgtcagga taaagtggat    37983
ctgctgcatc tcccagagag tgcatgtttt gcttttctaa tgttaatgga tttactgttt    38043
ttttcccccc ag g cca aat tca gat aat cga cgc cag ggt ggc aga gaa      38092
             Pro Asn Ser Asp Asn Arg Arg Gln Gly Gly Arg Glu
                         155                 160 aga ttg gcc agt acc aat gac aag gga agt atg gct atg gaa tct gcc     38140
Arg Leu Ala Ser Thr Asn Asp Lys Gly Ser Met Ala Met Glu Ser Ala
   165                 170                 175 aag gag act cgc tac tgt gca gtg tgc aat gac tat gct tca ggc tac     38188
Lys Glu Thr Arg Tyr Cys Ala Val Cys Asn Asp Tyr Ala Ser Gly Tyr
180                 185                 190                 195 cat tat gga gtc tgg tcc tgt gag ggc tgc aag gcc ttc ttc aag aga     38236
His Tyr Gly Val Trp Ser Cys Glu Gly Cys Lys Ala Phe Phe Lys Arg
                200                 205                 210 agt att caa g gtaatagtgt gttgaaaacg acttctattt ttgatcctat            38286
Ser Ile Gln gagcagatcc taagagccaa agcgactgag gaaggaagac atagaatcag ccatttgtac    38346
aaaacatgaa tccctagtag gtccactagt atctttggta gaaacatgga gaagagacag    38406
gatctcagga gaaggagttg acacatggca gggcagctga ggctgagtaa ttccgcttcc    38466
ttcctttggc aagactcaat cagtcttgag caactctaca gaagaattcc actagctgga    38526
tctctgagga aaaagaaat gttgtctgtg ccctgactgg ggaatgccag atggacattc     38586
atgtttggta ggcaactttg cctatatgat ctggtatatg ctgttaattg tccatgcata    38646
attatctctc tactcaggcc ttgtccaggc aaatattctg ttttgttcta gtttagcttg    38706
ttctcccctt tctctcttcc atctctttct tgtctcaatg gatgacagga tattttgcta    38766
tgagctgact cagtggttgg tgtcttgtaa tggggagata tcatctttat caaacagtta    38826
ttaagtatct acctgtagca tttcatttc ccgcctgcct ccattgtttt cttgtctata     38886
gtttgccaat tatagctaat atacggagag ctatacttta tttctactcc agaaatgtct    38946
ctattattgc attataatag gatacccctgg ggaaacacta atcatttta ctacctaaaa    39006 tacctatgct gaatatcctt tatctgatag gaacagagat ctgacagcag cttaggctaa    39066
ccaaattcat ttttatctt aagtgtgggg cattttctc tcttcttatt ctttacctt       39126 tcagcttaag tgaaggttag tataaacact aagaatattt ctgatggagt tttcatgtga    39186
ttccttctac aaaaacccag atttaagtaa cttgttgaaa accagagtcc gctaagttaa    39246
taaacactga ttgaagaagt gattctcatg gactttctgt gatagctctt tcctgccctg    39306
atatgagatg aaagctgggg gatggtatat agtatttatt tttccttccg ttgccagtgg    39366 gactttttt ttttttttaa aagctgttca tatcttaatc gagtagcatg tgaggtcaac      39426
atggtctatt ttaaaagcat tttcttcgac acattgcttt taacatcttt tagaactctg    39486
ctgtgagaca catggacttt tttgttggta tttttataca attaatgata ttctcaatag    39546
```

```
taatctttgt gtgtgtatat atatagaaat aaattctaaa tgtaagttaa tatatttatt    39606 attttttctaa acatatataa atatatatat gcacacaggc tatttaattt tattagatga   39666
tgctatttta attcagaaaa aaatgacatt tatatttga tttaggttag tataagccct     39726
tagaggtgtt ttgacaactc tcttaatttg tggttttact gtttatttga ttttatataa    39786
tctaaaatac cattgttttt accaagcatt taatttggca gtgaaagagc gtctgacaga    39846
ggtatggtta gtagataggt ctaactgcac aactggatgg attgagctga gactgtttcc    39906
tcatcagtaa aaatgatttg aagcagtggt tggcaaagtt tttctgtaaa gggccagata    39966
ataatatttt aggctttaca agggccatgc agtctctgtt gcagctaccg aactggatta    40026
tagcctgtaa ggtgacctgt aaacacatgg aagtgattat gtgctaataa aactttatt    40086 atcagaatag gtaacagatc agccctggcc cgtggccgat ccctgattta atgtttattt    40146
atctgatcta aatacctta tttatggaag ggaataggg ggattttaaat ctaaagtttt     40206 gattattcac attttactga gaacttactc tatacctgat tagatgttcc gagagaaata   40266 aaaaaaagt gtaagacata atccataata ccacaaaatt taaaatgtat ttaggaaatt     40326
tatttgagga agtaaatgta cttgttctca tgatacaatc agaaagtaag tcagtattga    40386
taaagtgtta cctgtatgag aaagataagg aaaacaatag agagatgtaa gaaatgaaaa    40446
taccagttat aaattaaaat tattaagatt gaaagtggaa atgatcttcc tccgagaaac    40506
aatggcaata ttctcacaaa ttttttacat cattttgtt cagcatttaa gataaaatta     40566
tataaattcc cataacattt agtattgtct ctaagcatta agaacagaaa aaacagaagg    40626
aaaatatatt tctaaaaatc aacgaataca gtgtgagatg tttcattggt atggcattat    40686
ctcaagttca aacattttga aaaatgtctg cttactcttt gatagttaaa aacaagtatc    40746
tcagctggcg tggtggctca ggcctgtaac cccagcagtt tgggaggctg aggcgagtgg    40806
atcacaaggt caggagatcg agaccatcct ggccaacatg gtgaaacccc atctctacta    40866
aaaatatgaa aattagctga gcgtggtggt gcacacctgt agtcccagct acttgggagg    40926
ctgaggcagg ataattgctt gaacctggga ggcagaggtt gcagtgagct gagatcatgc    40986
cactgccgtc cagcctggtg acagagtgag actccatctc aaaaaacaaa caaaacaaca    41046
ccaccaccac taacaaaaac ctcttatcgc cgtcttgtat acgcagacca gctagtagaa    41106
ttttactgaa acagtagcct ataaaaatgc aattccactt ggtttcagaa acttcttgtg    41166
tatcatagtg tgaagtcact tatcttaggc ttttaaaatg ggataaatat tgagtccaaa    41226
gttctggaag aagcctagaa agaaggcaga gttattaact tttagatata gggaggaacc    41286
ttaaaattat tcagttcttc attcattcac ttattcattg actagcttta ctaacaaagc    41346
cctatgcaag accctggaaa tgcaatgata gaaaaacctg gtccctaccc tcacagaact    41406
tgtgaggtaa agggggatac agactgataa accagcaatt gatgatggt gtcaagatag     41466 aggtgaaggc agtgtcttat aggatccaaa ctccactcag tcctggtggt ggttgagtct    41526
ggctatcaga ggtttcctga ttaaatctgg agggtgagtc aagggagcat ggtgaagaag    41586
gagggaatgc atgtttagcc atgtgaatga gtccatgagt gaagaccagg aggaaaggca    41646
gagcgcgggg aattctatgc gtaatattta acaaaattaa tgtactgtta aacaaagaca    41706
tttctgggcc atggatttaa tcctagactg tgtaaaaacc aagtaattga tttcctttat    41766 acttttaaaag catttccatg tatttgattt gtttgtgtgt ataaaaggga aataccacaa    41826
```

| | |
|---|---|
| caagtttaag ggtttctagt tctgctttct catcatagtc ttgataactt ggaactaaaa | 41886 |
| agtttttgct gaaattgtct gtgactcttt ataaatcaca ctgcccctca aacacattta | 41946 |
| aggatggtga agggtctgac acgtaggtgg gaagttctga agatgccgca gctc | 42000 |

GENETIC POLYMORPHISMS OF ESTROGEN RECEPTOR ALPHA ASSOCIATED WITH FAVORABLE RESPONSE TO HORMONE REPLACEMENT THERAPY

CROSS REFERENCE TO RELATED APPLICATIONS

This application claims the benefit of U.S. Provisional Application No. 60/270,700, filed on Feb. 22, 2001, the disclosure of which is incorporated herein by reference in its entirety.

FIELD OF THE INVENTION

The present invention concerns methods for beneficially increasing HDL cholesterol levels in subjects.

BACKGROUND OF THE INVENTION

Endogenous estrogen prior to menopause, and exogenous estrogen use after menopause, results in elevations of HDL cholesterol in women. This effect is often cited as a potential explanation for lower rates of heart disease in premenopausal women and postmenopausal women taking estrogen replacement. Sullivan et al., *Ann Intern Med* 1988; 108:358–363; and Gerhard et al., *Circulation* 1995; 92:5–8. However, there is considerable variability among women in terms of premenopausal HDL levels and changes in HDL in response to postmenopausal estrogen replacement. A significant portion of this variability has been attributed to genetic factors. Mahaney et al., *Arterioscler Thromb Vasc Biol* 1995; 15:1730–1739; and Austin et al., *Am J Hum Genet* 1998; 62:406–419. Allelic variants of the estrogen receptor alpha (ER-α) gene that alter the expression, function, or stability of the expressed receptor protein may account for some of this variation. Functionally significant mutations in other steroid receptor genes including receptors for androgens, mineralocorticoids, vitamin D, and glucocorticoids have already been described. Being able to identify women who are likely to have a more favorable lipid response to estrogen would be useful for patients and their physicians as they weigh the risks and benefits of estrogen replacement therapy.

SUMMARY OF THE INVENTION

A first aspect of the present invention is, accordingly, a method of screening a subject for increased likelihood of having a favorable response to estrogen replacement therapy, particularly with respect to cardiovascular health (e.g., improved future cardiovascular health as compared to that found in the same patient without estrogen replacement therapy; a decreased probability of heart disease (e.g., a decreased , heart disease (i.e., high density lipoprotein (HDL) level)). The method comprises detecting the presence of at least one estrogen receptor alpha polymorphism in the subject, the presence of the estrogen receptor alpha polymorphism indicating the subject is more likely to have a favorable response to estrogen replacement therapy.

Estrogen receptor alpha polymorphisms of interest herein (that is, polymorphisms the detection of which would indicate an increased likelihood of a favorable response to estrogen replacement therapy, are, in general, the rare form of estrogen receptor alpha polymorphisms, and in particular include the rare form of polymorphisms found in the first intron of the estrogen receptor alpha gene. Examples of suitable polymorphisms include the IVS1-1415 polymorphism (also called the CIT Intron 1 polymorphism, at a position 1415 base pairs before the beginning of exon 2), the IVS1-1505 polymorphism (also called the A/G Intron 1 polymorphism, at a position 1505 base pairs before the beginning of exon 2), the IVS1-401 polymorphism (also called the PvuII polymorphism (a C/T SNP)), and the IVS1-354 polymorphism (also called the XbaI polymorphism (an A/G SNP)). The detection of the polymorphism can include detecting whether or not the subject is heterozygous or homozygous for the polymorphism, and the detection step can also include detecting two or more different such polymorphisms in the subject.

A second aspect of the present invention is a method for beneficially affecting cardiovascular health, decreasing the risk of heart disease, and/or increasing HDL levels in a subject (e.g. beneficially altering the LDLIHDL ratio), the method comprising: (a) determining the presence of at least one estrogen receptor alpha polymorphism in said subject; and then, if said estrogen receptor alpha polymorphism is present, (b) administering estrogen replacement therapy to said subject in an amount effective to beneficially affect cardiovascular health, decrease the risk of heart disease, and/or increase HDL levels in said subject. Polymorphisms of interest are as discussed above.

A further aspect of the present invention is a method of treating a subject for depressed HDL levels (i.e., depressed in absolute levels or depressed relative to LDL levels), said method comprising the steps of: selecting a subject that carries at least one estrogen receptor alpha polymorphism, and administering estrogen replacement therapy to said subject in an amount effective to increase HDL levels (e.g., beneficially alter the LDL/HDL ratio) in said subject. Polymorphisms of interest are as discussed above.

A further aspect of the present invention is the use of one or more estrogen replacement therapy active agents for the preparation of a medicament for carrying out a method as described above.

A further aspect of the present invention is the use of a means of detecting an estrogen receptor alpha polymorphism of interest in determining if a subject is suitable for treatment with hormone replacement therapy for beneficially affecting cardiovascular health, decreasing risk of heart disease, and/or raising HDL levels in that subject. Polymorphisms of interest are the same as discussed above.

Still further aspects of the present invention include kits, reagents such as oligonucleotide probes, restriction enzymes and other such means for carrying out methods as described above, the use of such reagents for the preparation of kits or diagnostic reagents for carrying out the methods described above, the use of the estrogen receptor polymorphisms described above in structuring clinical trials of estrogen replacement therapy active agents for beneficial efficacy as discussed above, and the use of the estrogen receptor polymorphisms as targets for rational drug design.

The foregoing and other objects and aspects of the present invention are explained in greater detail in the drawings herein and the specification set forth below.

DETAILED DESCRIPTION OF THE PREFERRED EMBODIMENTS

Figure 1:
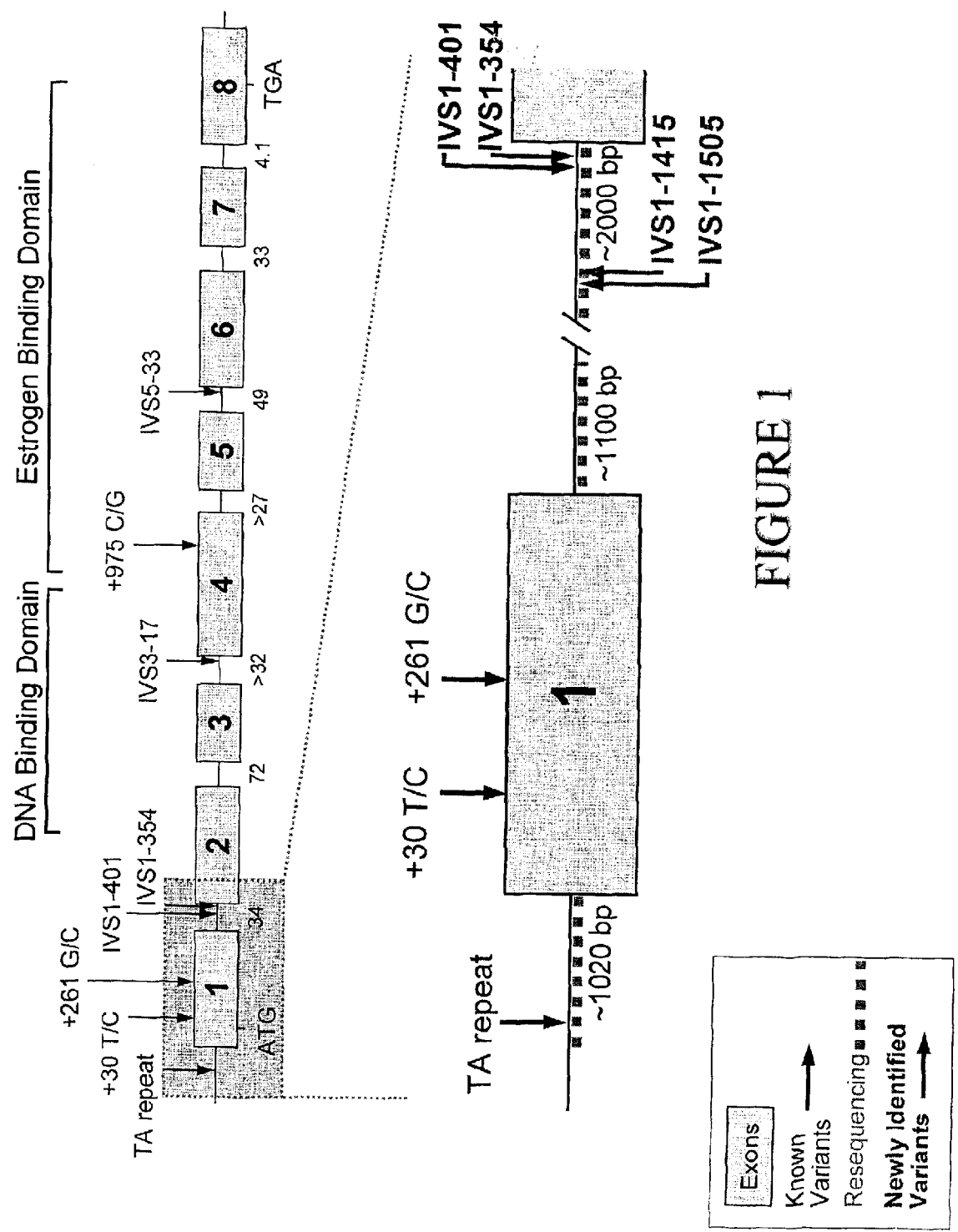
FIG. 1. The human estrogen receptor-α (ER-α) gene. Numbered boxes indicate exons. Vertical arrows indicate single nucleotide polymorphisms (SNPs) and the TA microsatellite repeat (above=previously recognized variants, below=new variants). Portions resequenced for novel SNP detection are indicated by dotted lines. Intronic regions (solid black lines) are not drawn to scale. Small numbers under each intron indicate the estimated size of the intron expressed as kilobase pairs.

As noted above, the method of the present invention is concerned with, among other things, determining whether a subject will have a favorable response to estrogen replacement therapy, for example with respect to cardiovascular health, heart disease, and/or HDL levels. A favorable response with respect to cardiovascular health may be, for example, improved future cardiovascular health as compared to that expected in the same patient without estrogen replacement therapy; lack of an unduly deleterious effect on cardiovascular health as compared to patients without the detected polymorphism, etc. A favorable response with respect to heart disease may be, for example, a decreased risk of heart disease as compared to that expected in the same patient without estrogen replacement therapy, lack of an unduly deleterious increase in risk of heart disease as compared to patients without the detected polymorphism, etc. A favorable response with respect to HDL levels may be, for example, an increase in HDL levels as compared to that expected in the same patient without estrogen replacement therapy, lack of an unduly deleterious decrease in HDL levels as compared to that found in patients without the detected polymorphism, etc. By "HDL levels" is meant both absolute HDL levels and relative HDL levels (e.g., an improved ratio of HDL to LDL).

Subjects for screening and/or treatment with the present invention are, in general, human subjects, and are preferably female subjects. The subject may be of any race and any age, including juvenile, adolescent, and adult, with adult subjects currently preferred, and post-menopausal, post-hysterectomy or other low estrogen subjects particularly preferred. The subject may also be a pre-menopausal female afflicted with low HDL levels. It will be appreciated by those skilled in the art that, while the present methods are useful for screening subjects to provide an initial indication of the suitability of a patient for a particular patient, this information will typically be considered by a clinician or medical practitioner in light of other factors and experience in reaching a final judgment as to the treatment which any given subject should receive.

An increase of high density lipoprotein (HDL) levels in a subject herein is meant both (i) an increase in absolute HDL levels and (ii) a relative increase in HDL levels as compared to low density lipoprotein (LDL) levels. The latter may be achieved by a decrease in absolute LDL levels, even where absolute HDL levels are substantially the same (or even decreasing, albeit to a lesser extent than a decrease in HDL levels).

1. Polymorphism Detection

In general, the step of detecting the polymorphism of interest may be carried out by collecting a biological sample containing DNA from the subject, and then determining the presence or absence of DNA containing the polymorphism of interest in the biological sample. Any biological sample which contains the DNA of that subject may be employed, including tissue samples and blood samples, with blood cells being a particularly convenient source. The nucleotide sequence of human estrogen receptor alpha is known and suitable probes, restriction enzyme digestion techniques, or other means of detecting the polymorphism may be implemented based on this known sequence in accordance with standard techniques. See, e.g., U.S. Pat. Nos. 6,027,896 and 5,767,248 to A. Roses et al. The human estrogen receptor alpha is known. The cDNA sequence is given at GENBANK accession number X03635 (SEQ ID NO: 1), the sequence of exon 1 is given at GENBANK accession number X03635, and the sequence of exon 2 is given at GENBANK accession number AF123494 (SEQ ID NO: 3). The estrogen receptor alpha gene has been mapped to q25.1-ter of chromosome 6. The gene spans a region 296 kilobases (kb) in size, and comprises of 8 exons and their intervening introns. The gene sequence is available in the literature or from public databases such as GenBank. See GenBank accession no. NT_023451.8, nucleotides c5,431,852–5,136,132, the disclosure of which is incorporated herein in its entirety.

The polymorphisms described herein can be detected in accordance with known techniques based upon the known sequence information of the human estrogen receptor alpha and the information provided herein. Novel genes described herein can be isolated from human sources based upon the information provided herein or produced by other means such as site-directed mutagenesis of known or available nucleic acids.

The least common allele or rare allele for the intron 1 polymorphisms described herein are preferred: That is, they provide a favorable indication of response to estrogen replacement therapy with respect to HDL levels. The IVS1-401 (or PvuII) and IVS1-354 (or XbaI) polymorphisms are known. For IVS1-401PvuII the rare allele is C. For IVS 1-354XbaI the rare allele is G.

The IVS1-1505 (or A/G intron 1) polymorphism (which is at a location 1505 base pairs before the start of exon 2) is newly described herein. G is the rare allele and hence preferred.

The IVS1-1415 (or C/T intron 1) polymorphism (which is at a location 1415 base pairs before the start of exon 2) is newly described herein. T is the rare allele and hence preferred.

Determining the presence or absence of DNA containing a polymorphism of interest may be carried out with an oligonucleotide probe labelled with a suitable detectable group, or by means of an amplification reaction such as a polymerase chain reaction or ligase chain reaction (the product of which amplification reaction may then be detected with a labelled oligonucleotide probe or a number of other techniques). Further, the detecting step may include the step of detecting whether the subject is heterozygous or homozygous for the polymorphism of interest. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

Amplification of a selected, or target, nucleic acid sequence may be carried out by any suitable means. See generally D. Kwoh and T. Kwoh, Am. Biotechnol. Lab. 8, 14–25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392–396 (1992); G. Walker et al., Nucleic Acids Res. 20, 1691–1696 (1992)), transcription-based amplification (see D. Kwoh et al., Proc. Natl. Acad Sci. USA 86, 1173–1177 (1989)), self-sustained sequence replication (or "3SR") (see J. Guatelli et al., Proc. Natl. Acad. Sci. USA 87, 1874–1878 (1990)), the Qβ replicase system (see P. Lizardi et al., BioTechnology 6, 1197–1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra).

DNA amplification techniques such as the foregoing can involve the use of a probe, a pair of probes, or two pairs of probes which specifically bind to DNA containing the polymorphism of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

In general, an oligonucleotide probe which is used to detect DNA containing a polymorphism of interest is an oligonucleotide probe which binds to DNA encoding that polymorphism, but does not bind to DNA that does not contain the polymorphism under the same hybridization conditions. The oligonucleotide probe is labelled with a suitable detectable group, such as those set forth below in connection with antibodies. Such probes are sometimes referred to as detection probes or primers herein.

Probes and primers, including those for either amplification and/or protection, are nucleotides (including naturally occurring nucleotides such as DNA and synthetic and/or modified nucleotides) are any suitable length, but are typically from 5, 6, or 8 nucleotides in length up to 40, 50 or 60 nucleotides in length, or more. Such probes and or primers may be immobilized on or coupled to a solid support such as a bead or chip in accordance with known techniques, and/or coupled to or labelled with a detectable group such as a fluorescent compound, a chemiluminescent compound, a radioactive element, or an enzyme in accordance with known techniques.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. When PCR conditions allow for amplification of all ApoE allelic types, the types can be distinguished by hybridization with allelic specific probe, by restriction endonuclease digestion, by electrophoresis on denaturing gradient gels, or other techniques.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

It will be readily appreciated that the detecting steps described herein may be carried out directly or indirectly. For example, a polymorphism could be detected by measuring by digestion with restriction enzymes, detection of polymorphic markers that are linked to the polymorphism, etc.

Kits useful for carrying out the methods of the present invention will, in general, comprise one or more oligonucleotide probes and other reagents for carrying out the methods as described above, such as restriction enzymes, optionally packaged with suitable instructions for carrying out the methods.

2. Estrogen Replacement Therapy.

"Estrogen replacement therapy" as used herein (sometimes also referred to as "hormone replacement therapy" or HRT) refers to a long-term therapy in which estrogen or estrogenic active agents are administered to a subject continuously over an extended period of time (e.g., one month, one year, or more) to maintain sustained blood levels of the active agent to combat the effects of menopause or hysterectomy (e.g., loss of calcium from bone and increased incidence of classical osteoporotic fractures of the forearm and hip, ischemic heart disease, etc.). The administration may be daily or periodically.

Estrogen replacement therapy may be carried out by any suitable means. All typically involve administering an active agent such as estrogen or an estrogen analog (typically a steroid that has estrogen activity) to the subject in an estrogen replacement therapy effective amount, which is generally commensurate with an amount effective to enhance IIDL levels as discussed above. Any suitable route of administration may be employed, including, but not limited to, oral administration, aerosol administration to airway surfaces, intravenous injection, subcutaneous injection, intramuscular injection, transdermal administration (e.g., a patch), etc. Oral and transdermal formulations are currently preferred. Numerous estrogen replacement therapy preparations and protocols are known, including but not limited to those described in U.S. Pat. Nos. 5,922,349; 5,897,539; 5,565,199; 5,468,736; 5,422,119; 5,288,717; and 5,023,084, the disclosures of all of which are incorporated by reference herein in their entirety. Other agents, such as progesterone (or progestin) in a hormone replacement therapy effective amount, may be administered along with the estrogen to provide a combination therapy, if desired (typically to reduce undesirable side-effects of estrogen monotherapy, as such estrogenic endometrial proliferation and corresponding risk of endometrial cancer).

Suitable active agents for estrogen replacement therapy include, but are not limited to, natural and synthetic estrogens such as conjugated equine estrogen, ethinyl estradiol, micronized estradiol, 17β estradiol, mestranol, estradiol valerate, 11-nitrato estradiol, 7-α-methyl-11-nitratoestradiol, piperazine estrone sulfate, quinestranol, and 8,9-dehydroestereone (particularly alkali metal salts and sulfate esters thereof). See, e.g., U.S. Pat. No. 5,422,119 at column 6; U.S. Pat. No. 5,288,717. Of course, all active agents may be prepared as a pharmaceutically acceptable salt or ester, in accordance with known techniques, The progestin component may be any progestationally active compound, including but not limited to progsterone, 17-hydroxyprogesterone, dihydroprogesterone, medroxyprogesterone acetate, norethindrone, norethindrone acetate, norethynodrel, ethynodioldiacetate, norgesterel, levonorgesterel, gestodene, delta-15-levonorgesterel, norgestimate, 17-deacetyl norgestimate, nomegestereol, nesterone, desogesterel and 3-keto-desogesteral. See, e.g., U.S. Pat. No. 5,422,119 at column 6.

In general, a pharmaceutical formulation or medicament for estrogen replacement therapy is prepared by bringing an effective amount of the active agent into contact with a pharmaceutically acceptable carrier, such as lactose or talc (for an oral administration), intimately admixing the two, and forming (when necessary) the mixture into a suitable unit dosage form such as a patch for transdermal administration or a tablet, dragee, capsule or pill for an oral dosage form.

The amount of active agent administered will depend upon factors such as the specific active agent, the age, weight and condition of the subject, the route of administration, etc. For example, the estrogenic active agent may be administered in an a amount of from 0.3 to 1.2 mg daily for orally administered conjugated equine estrogen; or from about 25 μg/day to about 150 μg/day of transdermal β-estradiol.

Examples of commercially available estrogen preparations include: Alora™ (skin patch), Climara™ (skin patch), Estraderm™ (skin patch), FemPatch™ (skin patch), Estrace™ (pill or skin patch), Estrab™ (pill), Menset™ (pill), Ogen™ (pill), Ortho-est™ (pill), and Premarin™ (pill)

Examples of commercially available estrogen/progestin combination formulations include, but are not limited to, Combipatch™ (skin patch) and Prempro™ (pill).

The new polymorphisms described herein provide novel nucleic acids encoding the human estrogen receptor alpha, along with probes such as described above that bind selectively thereto. Such nucleic acids can be inserted into vectors such as plasmids, optionally associated with or placed under the control of a promoter, and the nucleic acids may be inserted into host cells and optionally expressed therein (when the promoter is operative in the host cell) to produce estrogen receptor alpha. The nucleic acids and the encoded proteins may be used in accordance with known techniques, such as described in U.S. Pat. No. 6,222,015 to H. Wilkinson.

The present invention also provides a method of conducting a clinical trial on a plurality of human female patients. Such methods advantageously permit the refinement of the patient population so that advantages of particular treatment regimens (typically administration of pharmaceutically active organic compound active agents) can be more accurately detected, particularly with respect to particular subpopulations of patients. In general, such methods comprise administering a test hormone replacement therapy to a plurality of subjects (a control or placebo therapy typically being administered to a separate but similarly characterized plurality of subjects) and detecting the presence of at least one estrogen receptor alpha polymorphism as described above in the plurality of subjects. The polymorphisms may be detected before, after, or concurrently with the step of administering the test therapy. The influence of detected polymorphism on the test therapy can then be determined on any suitable parameter or potential treatment outcome or consequence, including but not limited to: (i) the efficacy of said hormone replacement therapy, (ii) a favorable response to said hormone replacement therapy with respect to cardiovascular health, (iii) a favorable response to said hormone replacement therapy with respect to risk of heart disease, and/or (iv) a favorable response to said hormone replacement with respect to HDL levels. Such determinations can be carried out in accordance with any suitable technique, including but not limited to those available from SAS, Inc., Cary, N.C., USA.

The present invention is explained in greater detail in the following non-limiting Examples.

EXAMPLE 1

In this example, we describe the association between several previously described and two newly identified sequence variants in the estrogen receptor-alpha gene and changes in HDL in response to treatment with estrogen replacement among women enrolled in the Estrogen Replacement and atherosclerosis (ERA) trial.

The ERA study population included 309 unrelated postmenopausal women with established coronary artery disease were enrolled at five clinical sites in the U.S. (Winston-Salem, Greensboro, and Charlotte, N. C.; Hartford, Conn.; and Birmingham, Ala.). Women with triglycerides>400 mg/dl, uncontrolled diabetes or hypertension, or excessive alcohol use were ineligible. Eligible women were randomized to receive daily oral estrogen (Premarin® 0.625 mg), estrogen plus progestin (medroxyprogesterone acetate [MPA]) 2.5 mg, or placebo and followed for an average of 3.2 years for progression of angiographically defined coronary disease. Plasma specimens obtained after overnight fasting were collected at baseline and annually thereafter for lipid and lipoprotein determinations. Buffy coats were separated from the baseline plasma specimens and frozen at−80° C. for subsequent genetic analyses. Data on other potential confounders, including age, race, BMI, and physical activity were collected using standardized questionnaires and procedures. Herrington et al., *Control Clin Trials* 2000; 21:257–285.

Lipid and Hepatic Lipase Analyses

Fasting plasma specimens for lipoprotein determinations were obtained. Cholesterol and triglycerides were measured in the WFU Lipid Analytic Laboratory on a Technicon RA-1000 autoanalyzer as described in the Technicon technical manual for cholesterol (SM4-0139A85) and for triglyceride (SM4-0189K87, glycerol phosphase-oxidase [GPO] blank method). The cholesterol method is based on the enzymatic cholesterol procedures of Allain et al., (*Clin Chem* 1974; 20:470), Roeschlau et al., (*Klin Chem Biochem*1974; 12:226) and the Trinder peroxidase/4-aminophenazone system. *Ann Clin Biol Chem* 1969; 6:24–27. The triglycerides method was described by Fossati and Principe. *Clin Chem* 1982; 28:2077. Total glycerides in plasma were quantitated. HDL cholesterol was measured using the heparin-manganese precipitation procedure. See, Burstein et. al., *Clin Chem Acta* 1960; 5:609; and Lipid Clinics Research Program: *Manual of Clinic Operations; volume 1: Lipid and lipoprotein analysis*, Bethesda, Md., DHHS; 1982 . . . LDL cholesterol was calculated using the Friedewald formula. Lp(a) measurements were made on a COBAS FARA II centrifugal autoanalyzer.

Hepatic lipase was measured after subjects (who had fasted overnight) were given an intravenous bolus infusion of 60 units heparin per kg body weight. Fifteen minutes later, the post-heparin sample was drawn into tubes containing EDTA on ice, the plasma promptly separated, aprotinin added, and the sample rapidly frozen at −70° C. Lipase activity was assayed using [$^3$H]triolein-labeled TRITION X-100™ emulsion as described previously, with the addition of 1 mol/L NaCl.

DNA Isolation and Genotyping

DNA was isolated from stored buffy coats using a standard guanidine thiocyanate procedure. Genotyping was performed for each single nucleotide polymorphism (SNP) using PCR followed by restriction enzyme digest (PCR-RFLP), allele-specific PCR (AS-PCR), or capillary electrophoresis (CE) on a 3700 DNA Analyzer (ABI, Inc., Foster City, Calif.). For the AS-PCR assays, a PCR reaction was performed with the external primer pair, followed by a second reaction with the allele-specific primer pair. PCR fragments from AS-PCR and PCR-RFLP assays were separated on 2% agarose gels and genotyped by the size of resulting fragments. For the CE assays, fluorescently labeled PCR fragments were diluted in water and run on 3700 DNA Analyzers. Genotypes were determined using Genotyper software (ABI, Inc.). SNPs located in coding regions are denoted using nucleotide number counted from the translation start site based on the Genebank reference sequence XM_045967.

DNA Sequencing and Analysis

In DNA from the 96 women with the highest or lowest HDL response to HRT, segments of the promoter region and the 5' and 3' regions of intervening sequence 1 (IVS1) were PCR-amplified and sequenced using the ABI BigDye Terminator sequencing kit. Sequencing products were analyzed on an ABI 3700 DNA Analyzer. DNA sequencing data were aligned and analyzed using Sequencher DNA analysis software (Gene Codes Corp., Ann Arbor, Mich.).

Statistical Analyses

The $\chi^2$ test was used to identify significant departures from Hardy-Weinberg equilibrium. Shuffling tests were performed to determine linkage disequilibrium between pairs of loci (Genetic Data Analysis, version 1.0215). Lipid and lipoprotein levels are presented as mean mean follow-up measurements obtained annually and at close-out. Generalized linear models were used to describe relationships among mean on-trial plasma lipids, estrogen treatment, and various genotypes after adjusting for: baseline lipid values and age; race (black, white, or other); diabetes (requiring medication); BMI (height [cm]/ weight$^2$ [kg]); smoking status at baseline (yes or no); physical activity (never, seldom [1–2 d/wk], sometimes [3–5 d/wk], often [5–7 d/wk]); and alcohol consumption (yes or no). Evidence for interaction was based on the nominal two-sided P-values from the F-test for the treatment by genotype interaction. For diallelic polymorphisms, P1 was used to indicate the less common, and P2 the more common, allele. Exploratory data analyses using additive, dominant, and recessive models revealed that carriers of the P2 allele for intron 1 polymorphisms (P1/P2 or P2/P2) responded similarly with respect to HDL and were therefore combined for some analyses. Effects of estrogen treatment were analyzed according to intention-to-treat, unless indicated otherwise. Exploratory data analyses revealed that the effect of genotype on lipid values during the trial was not different among women in the two active arms; therefore, these arms were collapsed unless otherwise indicated.

Results

FIG. 1 indicates the location of each polymorphism within the ER-α gene, including two novel SNPs in intron 1 (IVS 1) identified as a result of resequencing. The nine SNPs and the TA repeat polymorphism were in Hardy-Weinberg equilibrium. Frequencies for the variant SNP alleles ranged from 7.3% to 47.8% (Table 1). The distribution of TA repeats in the promoter region microsatellite ranged from 18 to 34 (median=26). The four SNPs in the 2 kb region 5' of exon 2 were in linkage disequilibrium with each other and with the two SNPs in exon 1 (P<10$^{-6}$) but not with SNPs located in intron 3, exon 4, or intron 5. The pattern of linkage disequilibrium was similar among white and black participants.

TABLE 1

Allele* and genotype frequencies (%) for each of the ER-α polymorphisms

| Allele or genotype | +30 T→C** (exon 1) n = 290† | +261 G→C (exon 1) n = 289 | IVS1-1505 A→G n = 298 | IVS1-1415 C→T n = 301 | IVS1-401 T→C n = 305 | IVS1-354 A→G n = 305 | IVS3-17 T10→T9 n = 269 | +975 C→G (exon 4) n = 301 | IVS5-33 T5→T4 n = 284 |
|---|---|---|---|---|---|---|---|---|---|
| P1 | 47.8 | 7.3 | 43.6 | 30.7 | 45.2 | 34.3 | 38.1 | 26.1 | 8.3 |
| P2 | 52.2 | 92.7 | 56.4 | 69.3 | 54.8 | 65.7 | 61.9 | 73.9 | 91.7 |
| P1/P1 | 21.7 | 1.0 | 17.4 | 7.6 | 18.9 | 9.3 | 15.2 | 7.3 | 0.7 |
| P1/P2 | 52.1 | 12.5 | 53.8 | 46.2 | 52.3 | 49.7 | 45.7 | 37.5 | 15.1 |
| P2/P2 | 26.2 | 86.5 | 30.2 | 46.2 | 28.8 | 41.1 | 39.0 | 55.1 | 84.2 |

*P1—less common allele, P2—more common allele
**(P2→P1)
†n = number of women

TABLE 2

Baseline and Mean On-trial HDL levels* (mg/dl) according to treatment arm and four ER-α intron 1 genotypes

| Genotype | Treatment | IVS1-1505 Baseline Mean (SE) | IVS1-1505 Follow-up Mean (SE) | IVS1-1415 Baseline Mean (SE) | IVS1-1415 Follow-up Mean (SE) | IVS1-401 Baseline Mean (SE) | IVS1-401 Follow-up Mean (SE) | IVS1-354 Baseline Mean (SE) | IVS1-354 Follow-up Mean (SE) |
|---|---|---|---|---|---|---|---|---|---|
| P1/P1 | HRT | 48.9 (3.0) | 60.7 (3.0) | 45.0 (4.0) | 59.4 (4.0) | 47.4 (2.9) | 60.4 (2.9) | 45.1 (3.5) | 59.8 (3.5) |
|  | Placebo | 48.6 (3.3) | 48.6 (3.4) | 48.1 (4.7) | 48.5 (5.0) | 47.6 (3.1) | 47.9 (3.2) | 46.9 (4.3) | 48.1 (4.5) |
| P1/P2 | HRT | 46.2 (2.2) | 52.6 (2.2) | 48.5 (2.3) | 55.1 (2.3) | 47.2 (2.1) | 53.1 (2.2) | 48.3 (2.2) | 54.6 (2.3) |
|  | Placebo | 44.8 (2.6) | 47.2 (2.7) | 44.2 (2.7) | 46.2 (2.8) | 44.4 (2.6) | 47.7 (2.6) | 45.5 (2.6) | 48.2 (2.6) |
| P2/P2 | HRT | 44.8 (2.5) | 50.2 (2.5) | 45.1 (2.2) | 51.4 (2.3) | 42.8 (2.5) | 48.8 (2.5) | 44.9 (2.3) | 51.1 (2.3) |
|  | Placebo | 44.3 (3.0) | 45.5 (3.2) | 47.7 (2.6) | 49.0 (2.7) | 44.6 (3.0) | 45.2 (3.1) | 46.1 (2.8) | 47.0 (2.8) |
| Interaction p-values |  |  |  |  |  |  |  |  |  |
| Additive model** |  | 0.0196 |  | 0.1975 |  | 0.0093 |  | 0.0507 |  |
| Dominant model+ |  | 0.0049 |  | 0.0739 |  | 0.0036 |  | 0.0175 |  |

*After adjustment for age, race, BMI, diabetes, exercise, alcohol intake, and smoking
**(P1/P1 vs P1/P2 vs P2/P2) × treatment arm
+(P1/P1 vs P1/P2 and P2/P2) × treatment arm. In this model, P2 treated as a dominant allele Increases in HDL level with HRT were greatest in women who were homozygous for the less common (P1) intron 1 alleles. P values for the HRT by genotype interactions using dominant models ranged from 0.0036 to 0.0739 (Table 2). When expressed as percent change from baseline, homozygotes for the less common intron 1 alleles experienced a 24% to 33% increase in HDL with HRT compared with a 13% increase in carriers of more common alleles. Baseline HDL levels were slightly higher in IVS 1-401 C/C and IVS1-1505 G/G women compared with women with the IVS1-401 T/T and IVS1-1505 A/A genotypes, respectively (P=0.052 and 0.063).

Figure 2:
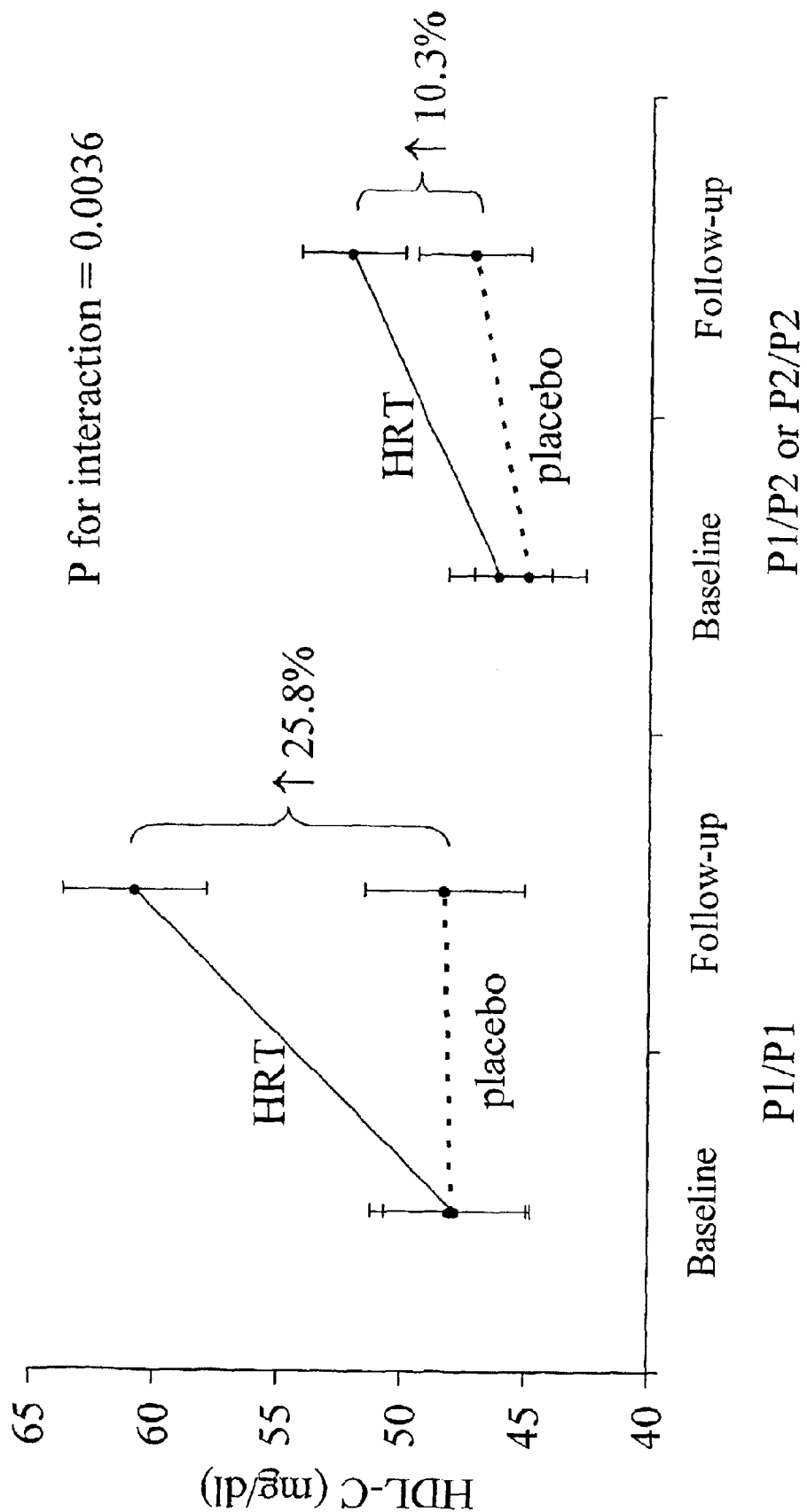
FIG. 2. Baseline and follow-up high-density lipoprotein cholesterol (HDL-C) among women in the ERA trial by active arms vs placebo and ER-α IVS 1-401 genotype adjusted for age, race, body mass index, diabetes, smoking, exercise, and alcohol intake. P value is for the HRT by genotype interaction. HRT=hormone replacement therapy.

Among the four intron 1 SNPs, evidence for interaction was greatest for the IVS1-401 polymorphism (FIG. 2). Women with the IVS1-401 C/C genotype who were assigned to HRT had a 13.1 mg/dl increase in HDL compared with a 6.0 mg/dl increase in women with the C/T or T/T genotypes (P value for HRT by IVS 1-401 interaction= 0.0036). In analyses limited to women who took ≧80% of their study medication, the interaction was even more pronounced (P=0.0004). Evidence of interaction was also present within each of the two randomly assigned active treatment arms (change in HDL by treatment and IVS 1-401 status: estrogen, C/C 26.0%, C/T or T/T 14.9%; estrogen plus progestin, C/C 29.0%, C/T or T/T 11.1%; P for interaction=0.029 and 0.007, respectively). When subjects were stratified into non-Hispanic whites (n=221), African-Americans (n=33), and others (n=11), the pattern was preserved in all three groups, although only non-Hispanic whites were sufficiently numerous to support an inference of interaction with confidence (P=0.023 for IVS 1-401 C/C versus C/T or T/T).

Figure 3:
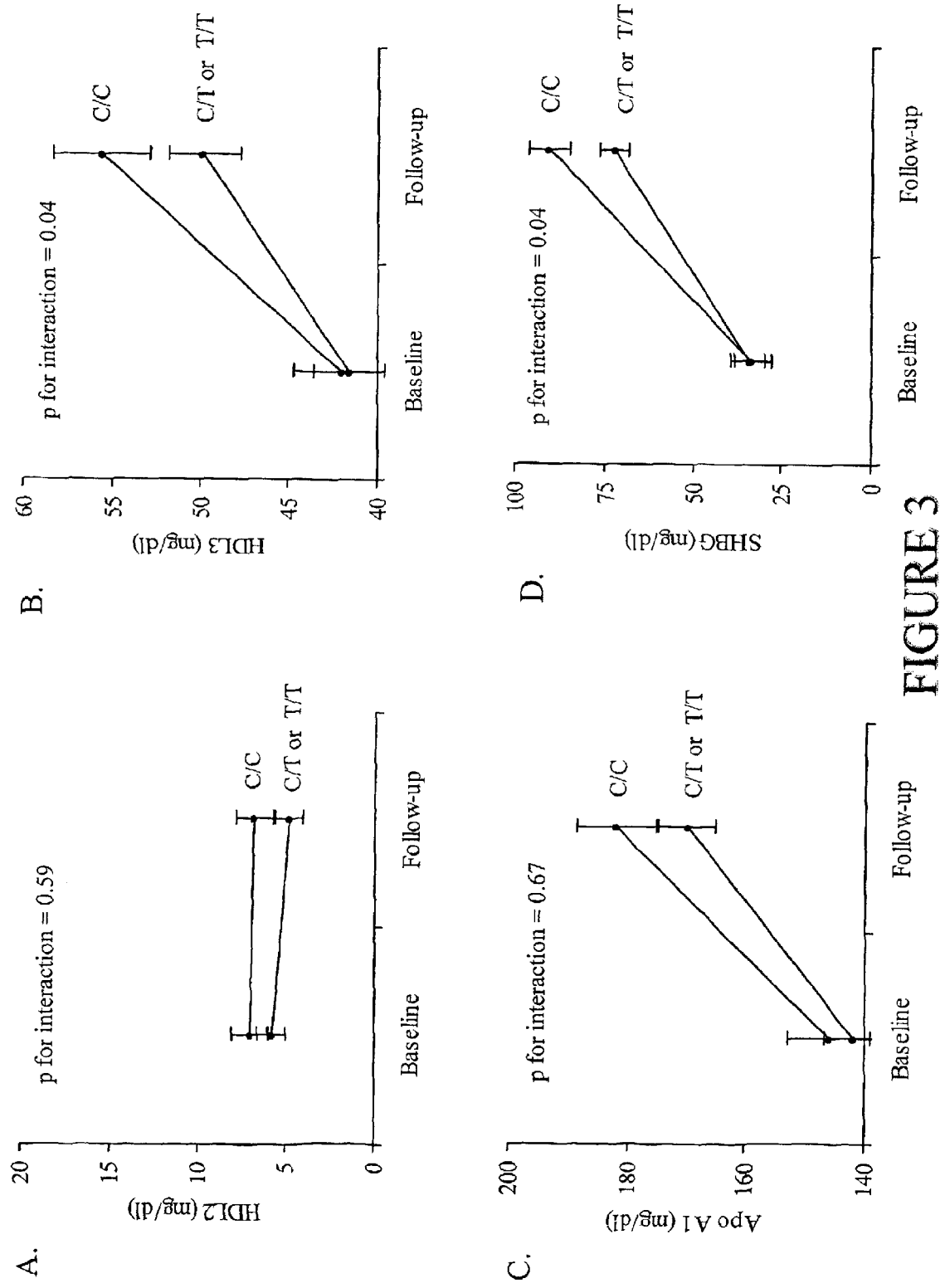
FIGS. 3A–D. Baseline and follow-up levels of $HDL_2$ (panel A), $HDL_3$ (panel B), Apo A-I (panel C), and sex hormone-binding globulin (SHBG) (panel D) in ERA women on active therapy stratified by IVS1-401 genotype. Results from women on placebo not shown. Results are expressed as group means with error bars indicating standard errors. P values are for the treatment by genotype interaction after adjusting for potential confounders.

In women on HRT with the IVS1-401 C/C genotype, $HDL_3$ increased by 13.6 mg/dl compared with 8.2 mg/dl in women with the C/T or T/T genotypes (P for interaction= 0.04) (FIG. 3). In contrast, there was no effect of the IVS1-401 genotype on response of $HDL_2$ to HRT. HRT-associated increases in Apo-AI were also greatest for IVS1-401 C/C women (FIG. 3); however, this increase was not significantly different than the increase observed in C/T or T/C women (36 mg/dl versus 28 mg/dl, P for interaction= 0.68). Similarly, the numerically greater reductions in LDL and ApoB among IVS1-401 C/C women were not sufficiently large to support an inference of interaction (data not shown). At the end of the trial, hepatic lipase levels were slightly lower in IVS1-401 C/C women compared to C/T or T/T women (P=0.06). However, there was no evidence of interaction with HRT (change in hepatic lipase with HRT relative to placebo: C/C 1.4 mg/dl, C/T or T/T 2.0 mg/dl; P for interaction=0.78). On the other hand, examination of another estrogen-sensitive protein produced in the liver, sex hormone-binding globulin, also revealed a significant HRT by IVS1-401 interaction (P for interaction=0.001) (FIG. 3).

Despite the favorable effects on HDL levels, progression of angiographically defined coronary disease was not significantly different among women with the IVS1-401 C/C genotype on HRT compared to the other women assigned HRT; although, the power to detect such an interaction for the angiographic endpoint was extremely limited. None of the other ER-α polymorphisms examined, including several different classifications of the promoter TA repeat, was associated with change in HDL cholesterol in response to HRT.

Discussion

The estrogen receptor is a ligand-activated factor that augments gene transcription by binding to specific DNA response elements. The human estrogen receptor gene, located at 6q24. 1, has been cloned, sequenced, and expressed in a variety of cell lines, and site-directed mutagenesis has identified domains which are highly conserved across species that are responsible for hormone or DNA binding and transcriptional activation. See, e.g. Ponglikitmongkol et al., *EMBO J* 1988; 7:3385–3388. Numerous naturally occurring sequence variants have also been identified, and their association with a variety of estrogen-dependent clinical phenotypes, including risk, age of onset, and estrogen-receptor status in breast cancer; spontaneous abortion, bone mineral density, body mass index, and hypertension have been examined.

A thymine-adenine (T-A) repeat has been identified in the genomic region 1174 bp 5' of exon 1. Piva et al., *Biochem Biophys Res Commun* 1992; 183:996–1002; and del Senno et al., *Hum Mol Genet* 1992;1:354. This microsatellite marker contains 10–27 T-A repeats that range in allelic frequency from <1% to 18%. Several investigators have also examined the relationship between ER polymorphisms and plasma lipids or atherosclerosis. Matsubara et al, in a study of 87 men and women, found no association between the XbaI or PvuII polymorphisms and plasma lipids or angiographically documented coronary disease. *Arterioscler Thromb Vasc Biol* 1997; 17:3006–3012. In another study, Kikuchi et al found that among 102 Japanese children aged 10 to 15 years, those homozygous for the XbaI polymorphism had significantly higher levels of LDL and apoB. *Acta Paediatr* 2000; 89:42–45. No association was evident with the PvuII polymorphism. In both studies, there was no apparent association with HDL levels, although the numbers of subjects were small and the analyses were not stratified by gender or estrogen use. In another study of 119 men undergoing coronary angiography, those with more severe disease or prior history of myocardial infarction were more likely to have greater numbers of T-A repeats in the promoter region microsatellite marker. In contrast, in the current study both the XbaI and the PvuII polymorphisms and two novel polymorphisms, all in high degree of linkage disequilibrium with each other, were associated in varying degrees with baseline HDL level and even more dramatically with the response of HDL to estrogen treatment.

Only one previously published study has described the association between ER polymorphisms and estrogen-dependent phenomena among women taking estrogen replacement. In a study of 248 Korean women, Han et al determined XbaI and PvuII genotype and measured bone mineral density before and after one year of hormone replacement therapy. *Osteoporosis Int*1999; 9:290–295. Although the differences were not statistically significant, the women who were homozygous for the XbaI or PvuII mutant alleles had higher BMD at baseline and less change over 1 year than women with one or two copies of the wild-type allele. Taken together, the data are consistent with the possibility that women with one of these polymorphisms are more responsive to endogenous or exogenous estrogen than other women.

It is not clear by what means the intron 1 polymorphisms are related to regulation of HDL levels. Hill et al. (*Cancer Res*1989; 49:145–148) reported that the estrogen-receptor protein was less frequently expressed in breast cancer cells that were homozygous for the PvuII mutant allele; however, Yaich et al failed to find a similar relationship in a larger study of 257 cases of primary breast cancer. *Cancer Res*1992; 52:77–83. Parl et al also found no correlation between the PvuII polymorphism and ER binding in breast cancer biopsy specimens. *Breast Cancer Treat Res*1989; 14:57–64. Whether intron 1 polymorphisms could directly influence the transcription, splicing, stability, or function of the downstream products of the estrogen receptor gene, or be linked to other causative sequence variants in other locations, remains unknown. Likewise, the elements of HDL regulation that vary according to genotypes are not fully examined in this study. The significant increase in Apo A-I levels with estrogen treatment in those women with the favorable genotypes could be consistent with augmented Apo A-I synthesis through greater activation of the estrogen response element in the promoter region of this gene. However, elevated levels of HDL cholesterol are presumably due to greater downregulation of hepatic lipase and impaired removal of cholesterol ester from circulating HDL particles. Without more detailed studies of HDL kinetics, it is impossible to know if the augmented responses to estrogen treatment would produce a net benefit in terms of reverse cholesterol transport and pathogenesis of atherosclerosis.

EXAMPLE 2

ESR1 Analysis

TA repeat–1020bp before exon 1

–1381 before the start codon

Novel SNPs:

A/G–1505 bp before exon 2

C/T–1415 bp before exon 2

Pvu II–401 bp before exon 2

Xba I–354 bp before exon 2

Regions sequenced:

–2246 to +53 bp around exon 2 currently sequencing–1324 bp to –259 bp before exon 1

+489–+1651 after exon 1

Estimated gaps:

E1

34 kb

E2

Est 72 kb(?)

E3

??

E4

??

E5

49 kb

E6

33 kb

E7

4.1 kb

E8

Primers for PCR:

```
5' REGION OF EXON 1:

ESR1-PR1-F    GCTTCAGCTACATTTGCATATTG          (SEQ ID NO: 4)
ESR1-PR1-R    ACCTCAGGTCACGAACCAAAG            (SEQ ID NO: 5)

ESR1-PR2-F    CCGAGAAGATCGAGTTGTAGGAC          (SEQ ID NO: 6)
ESR1-PR2-R    TCCTCGTTGGCTAGAAATACG            (SEQ ID NO: 7)

REGION AROUND EXON 2:

ESR-3F        GGTGGTGAAATGGAAAGAGATG           (SEQ ID NO: 8)
ESR-3R        ATATTGGCCCAGGACTTGGCAG           (SEQ ID NO: 9)

ESR-4-2F      CACAGGAACCTTCACTCCATC            (SEQ ID NO: 10)
ESR-4-2R      GCAGAGAAGTCCAACAAAGCA            (SEQ ID NO: 11)
(ESRA-2F and ESR-4-2R are the Primer pairs used to amplify the
region containing the SNPs at -1415 and -1505 from the start
```

-continued
of exon 2)

| ESR-5F | CATTGGTCTCTAATGGTTCTGAA | (SEQ ID NO: 12) |
| --- | --- | --- |
| ESR-5R | TCTCCATGTTTCTACCAAAGATAC | (SEQ ID NO: 13) |
| ER1 | TCTTTCTCTGCCACCCTGGCGTCGATTATCTGA | (SEQ ID NO: 14) |
| ER2 | CTGCCACCCTATCTGTATCTTTTCCTATTCTCC | (SEQ ID NO: 15) |

REGION IN INTRON 1, 3' OF EXON1:

| ESR-I1-1R | TGGGCTGGCAGGAGATTA | (SEQ ID NO: 16) |
| --- | --- | --- |
| ESR-I1-1F | GCTGCGTTCAGAGTCAARTTC | (SEQ ID NO: 17) |
| ESR-I1-2R | GGCTGAAGATGCACACTGAAT | (SEQ ID NO: 18) |
| ESR-I1-2BF | CTGGCATGTGACTTCTGACAG | (SEQ ID NO: 19) |

SEQUENCING PRIMERS:

| ESR2-SEQF | TGCCACCCTATCTGTATCTTTTC | (SEQ ID NO: 20) |
| --- | --- | --- |
| ESR2-SEQMF1 | ATCATAGCCTACTGCAGCCTC | (SEQ ID NO: 21) |
| ESR2-SEQMR1 | AATTAGCTGAGAATGGTGATGTGT | (SEQ ID NO: 22) |
| ESR2-SEQMR2 | ACAATTATTTCAGAACCATTA | (SEQ ID NO: 23) |
| ESR2-SEQR | CTTTCTCTGCCACCCTGGCGT | (SEQ ID NO: 24) |

EXAMPLE 3

Intron 1

Intron 1 of the estrogen receptor alpha gene is 34.2 kb in size (SEQ ID NO: 25). The SNPs described herein reside in the last 1.6 kb of intron 1, before the start of Exon 2.

The foregoing is illustrative of the present invention, and is not to be construed as limiting thereof. The invention is defined by the following claims, with equivalents of the claims to be included therein.

That which is claimed is:

1. A method of screening a human female for increased likelihood of having a favorable response to estrogen replacement therapy with respect to cardiovascular health due to increased HDL levels, comprising:

detecting the presence of at least one estrogen receptor alpha polymorphism in said subject, wherein said at least one estrogen receptor alpha polymorphism is selected from the group consisting of the IVS1-354 polymorphism, the IVS1-401 polymorphism, the IVS1-1415 polymorphism, and the IVS1-1505 polymorphism, the presence of said IVS1-354 polymorphism, IVS1-401 polymorphism, IVS1-1415 polymorphism, or IVS1-1505 polymorphism indicating that said subject is more likely to have a favorable response to estrogen replacement therapy with respect to cardiovascular health than a subject with other known estrogen receptor alpha polymorphisms.

2. A method according to claim 1, wherein said detecting step further comprises detecting whether said subject is homozygous for said at least one estrogen receptor alpha polymorphism.

3. The method according to claim 1, wherein the IVS1-354 polymorphism is a guanine.

4. The method according to claim 1, wherein the IVS1-401 polymorphism is a C/C genotype.

5. The method according to claim 1, wherein the IVS1-1415 polymorphism is a guanine.

6. The method according to claim 1, wherein the IVS1-1505 polymorphism is a thymine.

* * * * *